United States Patent
Lavin et al.

(10) Patent No.: US 12,356,113 B1
(45) Date of Patent: *Jul. 8, 2025

(54) WEB ENABLED AUDIOVISUAL MEDICATION DISPENSING WITH ENHANCED COMPLIANCE VERIFICATION

(71) Applicant: Omcare Inc., Burnsville, MN (US)

(72) Inventors: Lisa Lavin, Prior Lake, MN (US); Avery W. Weigle, Robbinsdale, MN (US); Darren S. Jeseritz, Savage, MN (US); Caleb O. Vainikka, Waconia, MN (US)

(73) Assignee: Omcare Inc., Burnsville, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/457,306

(22) Filed: Aug. 28, 2023

Related U.S. Application Data

(63) Continuation of application No. 16/994,463, filed on Aug. 14, 2020, now Pat. No. 11,743,424, which is a
(Continued)

(51) Int. Cl.
*H04N 7/14* (2006.01)
*A61J 7/04* (2006.01)
(Continued)

(52) U.S. Cl.
CPC ............ *H04N 7/142* (2013.01); *A61J 7/0427* (2015.05); *G07F 9/006* (2013.01); *G16H 20/13* (2018.01);
(Continued)

(58) Field of Classification Search
CPC ... G07F 17/0092; A61J 2200/30; G16H 20/13
See application file for complete search history.

(56) References Cited

U.S. PATENT DOCUMENTS

| 3,732,544 A | 5/1973 | Obland |
| 4,360,125 A | 11/1982 | Martindale et al. |

(Continued)

FOREIGN PATENT DOCUMENTS

| WO | WO 98/20439 A1 | 5/1998 |
| WO | WO 2020/018579 A1 | 1/2020 |

OTHER PUBLICATIONS

Tabsafe User Manual, Oct. 2010. Model 102. Revison E, 64 pages. Retrieved Apr. 26, 2018 https://www.tabsafe.com/wp-content/uploads/2018/03/TabSafe-Model-102-User-Guide.pdf.
(Continued)

*Primary Examiner* — Timothy R Waggoner
(74) *Attorney, Agent, or Firm* — Albert W. Watkins

(57) ABSTRACT

A web enabled audiovisual medication dispenser has a locked, tamper resistant housing; timers and alarms; a receptacle for aggregated medication pouches; and a cutter that separates the aggregated medication pouches from a strip. The cutter is also configured to notch a pouch to facilitate opening by a patient, and further configured to form a part of the tamper resistance. A medication pouch receptacle receives the one or more aggregated medication pouches cut from the strip. A first imaging apparatus displays the medication pouch receptacle and communicates the image at least to a remote apparatus for compliance. A second imaging apparatus displays from at least adjacent to the medication pouch receptacle to the patient, and captures an image of the patient handling and taking the medication from the pouch. The images may be analyzed automatically or by a remote caregiver, and are stored in an electronic medical record for compliance validation.

19 Claims, 13 Drawing Sheets

Related U.S. Application Data continuation-in-part of application No. 29/677,036, filed on Jan. 16, 2019, now Pat. No. Des. 904,007.

(51) Int. Cl.

| | |
|---|---|
| *G07F 9/00* | (2006.01) |
| *G16H 20/13* | (2018.01) |
| *G16H 80/00* | (2018.01) |
| *H04N 23/51* | (2023.01) |
| *H04R 1/02* | (2006.01) |
| *H04R 1/08* | (2006.01) |
| *H04R 3/00* | (2006.01) |

(52) U.S. Cl.
CPC ............. *G16H 80/00* (2018.01); *H04N 23/51* (2023.01); *H04R 1/028* (2013.01); *H04R 1/08* (2013.01); *H04R 3/00* (2013.01)

(56) References Cited

U.S. PATENT DOCUMENTS

| | | | |
|---|---|---|---|
| 4,616,316 A | 10/1986 | Hanpeter et al. | |
| 4,653,009 A | 3/1987 | Brown | |
| 4,695,954 A | 9/1987 | Rose et al. | |
| 5,630,347 A | 5/1997 | Elvio | |
| 5,646,912 A | 7/1997 | Cousin | |
| 5,713,485 A | 2/1998 | Liff et al. | |
| D392,843 S | 3/1998 | Mulvihill | |
| 5,752,621 A | 5/1998 | Passamante | |
| D404,200 S | 1/1999 | Ducusin et al. | |
| 5,890,656 A | 4/1999 | Fuhlbrigge | |
| 5,945,651 A | 8/1999 | Chorosinski et al. | |
| 6,004,020 A | 12/1999 | Bartur | |
| D427,594 S | 7/2000 | Lai | |
| 6,263,259 B1 | 7/2001 | Bartur | |
| 6,394,306 B1 | 5/2002 | Pawlo et al. | |
| D459,987 S | 7/2002 | Christianson | |
| 6,415,202 B1 | 7/2002 | Halfacre | |
| 6,527,138 B2 | 3/2003 | Pawlo et al. | |
| 6,529,801 B1 | 3/2003 | Rosenblum | |
| 6,539,281 B2 | 3/2003 | Wan et al. | |
| 6,594,549 B2 | 7/2003 | Siegel | |
| 6,607,094 B2 | 8/2003 | MacDonald | |
| 6,615,107 B2 | 9/2003 | Hubicki | |
| 6,625,518 B2 | 9/2003 | Depeursinge | |
| D483,755 S | 12/2003 | Arnold et al. | |
| 6,697,704 B2 | 2/2004 | Rosenblum | |
| 6,732,884 B2 | 5/2004 | Topliffe et al. | |
| 6,766,218 B2 | 7/2004 | Rosenblum | |
| D497,465 S | 10/2004 | Hradisky | |
| 6,957,126 B2 | 10/2005 | Kim | |
| 6,961,285 B2 | 11/2005 | Niemiec et al. | |
| D518,041 S | 3/2006 | Sun | |
| 7,155,202 B2 | 12/2006 | Helal | |
| 7,264,136 B2 | 9/2007 | Willoughby et al. | |
| D555,893 S | 11/2007 | Mulaw | |
| 7,359,765 B2 | 4/2008 | Varvarelis et al. | |
| 7,369,919 B2 | 5/2008 | Vonk et al. | |
| 7,440,817 B2 | 10/2008 | Fu | |
| 7,654,230 B2 | 2/2010 | Kroll | |
| 7,711,449 B2 | 5/2010 | Abdulhay et al. | |
| 7,801,745 B2 | 9/2010 | Walker et al. | |
| 7,873,435 B2 | 1/2011 | Yuyama et al. | |
| 7,878,152 B2 | 2/2011 | Kroll | |
| 7,917,246 B2 | 3/2011 | Handfield et al. | |
| 7,946,448 B1 | 5/2011 | Madey | |
| 7,963,201 B2 | 6/2011 | Willoughby et al. | |
| 7,991,507 B2 | 8/2011 | Liff et al. | |
| 8,019,471 B2 | 9/2011 | Bogash et al. | |
| 8,060,249 B2 | 11/2011 | Bear et al. | |
| 8,175,746 B2 | 5/2012 | Godlewski | |
| 8,196,774 B1 | 6/2012 | Clarke et al. | |
| 8,201,522 B2 | 6/2012 | Kroll | |
| 8,224,483 B1 | 7/2012 | Ansari et al. | |
| 8,453,874 B2 | 6/2013 | Simpson et al. | |
| 8,600,548 B2 | 12/2013 | Bossi et al. | |
| 8,600,549 B2 | 12/2013 | Park | |
| D699,758 S | 2/2014 | Lavin et al. | |
| 8,757,435 B2 | 6/2014 | Van Oort et al. | |
| 9,202,011 B2 | 12/2015 | Lavin | |
| D773,175 S | 12/2016 | Fagen | |
| D781,064 S | 3/2017 | Brownley et al. | |
| D812,246 S | 3/2018 | Hommel et al. | |
| D828,013 S | 9/2018 | Van Wijngaarden et al. | |
| 10,078,732 B2 | 9/2018 | Lavin | |
| D834,301 S | 11/2018 | Poissant | |
| 10,279,985 B2 | 5/2019 | Mills et al. | |
| 10,327,995 B2 | 6/2019 | Wang et al. | |
| 10,343,806 B2 | 7/2019 | Fagen et al. | |
| 10,347,377 B1 | 7/2019 | Lavin | |
| 11,464,710 B2 | 10/2022 | Mathew | |
| 11,743,424 B1 | 8/2023 | Lavin et al. | |
| 2001/0054071 A1 | 12/2001 | Loeb | |
| 2002/0113077 A1 | 8/2002 | Topliffe et al. | |
| 2002/0153411 A1 | 10/2002 | Wan et al. | |
| 2005/0259641 A1 | 11/2005 | Beninato et al. | |
| 2006/0161295 A1 | 7/2006 | Yun | |
| 2006/0184271 A1 | 8/2006 | Loveless | |
| 2006/0276931 A1 | 12/2006 | Walker et al. | |
| 2008/0105588 A1 | 5/2008 | Tran et al. | |
| 2009/0022293 A1 | 1/2009 | Routt | |
| 2009/0105876 A1 | 4/2009 | Simpson et al. | |
| 2009/0315702 A1 | 12/2009 | Cohen Alloro et al. | |
| 2010/0026817 A1 | 2/2010 | Ryan et al. | |
| 2010/0076595 A1 | 3/2010 | Nguyen | |
| 2010/0152885 A1 | 6/2010 | Regan et al. | |
| 2010/0164716 A1 | 7/2010 | Estevez et al. | |
| 2010/0194976 A1 | 8/2010 | Smith et al. | |
| 2010/0256808 A1 | 10/2010 | Hui | |
| 2011/0068115 A1 | 3/2011 | Choi et al. | |
| 2011/0080459 A1 | 4/2011 | Kroll | |
| 2011/0115875 A1 | 5/2011 | Sadwick et al. | |
| 2011/0202174 A1 | 8/2011 | Bogash et al. | |
| 2012/0081225 A1 | 4/2012 | Waugh et al. | |
| 2012/0083666 A1 | 4/2012 | Waugh et al. | |
| 2012/0101630 A1 | 4/2012 | Daya et al. | |
| 2012/0323360 A1 | 12/2012 | Lavin | |
| 2014/0005826 A1 | 1/2014 | Apell et al. | |
| 2014/0309769 A1 | 10/2014 | Wu et al. | |
| 2016/0001955 A1 | 1/2016 | Wang et al. | |
| 2016/0055318 A1 | 2/2016 | Lavin | |
| 2016/0324727 A1 | 11/2016 | Waugh et al. | |
| 2018/0029779 A1 | 2/2018 | Go | |
| 2018/0177684 A1* | 6/2018 | Deacon | G16H 40/67 |
| 2020/0253828 A1 | 8/2020 | Mathew | |
| 2020/0345587 A1 | 11/2020 | Aon et al. | |
| 2022/0058439 A1* | 2/2022 | Lee | G16H 20/10 |
| 2022/0105008 A1 | 4/2022 | Long et al. | |
| 2022/0254470 A1 | 8/2022 | LaFauci et al. | |

OTHER PUBLICATIONS

Phillips Lifeline 2016 Automated Medication Dispensing Service, 11 pgs, Retrieved Apr. 26, 2018 https://www.lifeline.phillips.com/pill-dispense/health-mdp.html.

Lumma, 2018. Smart Pill Dispenser. 25 pgs, Retrieved Apr. 26, 2018 https://www.kickstarter.com/projects/402921688/lumma-automated-medication-sorter-and-dispenser.

Imageware Systems, 2016. The pillphone. 2 pgs, retrieved Apr. 26, 2018 https://www.iwsinc.com/wp-content/uploads/2018/01/IWS-PillPhone-Brochure.pdf.

Spencer health Systems, 2018. Hello Im Spencer. 4 pgs, retrieved Apr. 26, 2018 https://www.helloimspencer.com/how-spencer-works/.

Livi, 2018 Livi Features. 6 pgs, Retrieved Apr. 26, 2018 https://liviathome.com/features.

Karen Zita Haigh PhD, Liana M. Kiff & Geoffrey Ho PhD, 2006. The Independent LifeStyle Assistant: Lessons Learned, Assistive technology, 18:1, 87-106 https://www.tandfonline.com/doi/abs/10.1080/10400435.2006.10131909, 6 pgs.

(56) References Cited

OTHER PUBLICATIONS

Honeywell. Haigh, Karen Zita. Oct. 29, 2005. The Role of intelligent Technology in Eldercare. www.htc.honeywell.com/projects/ilsa/ Retrieved Apr. 26, 2018, 55 pgs.

* cited by examiner

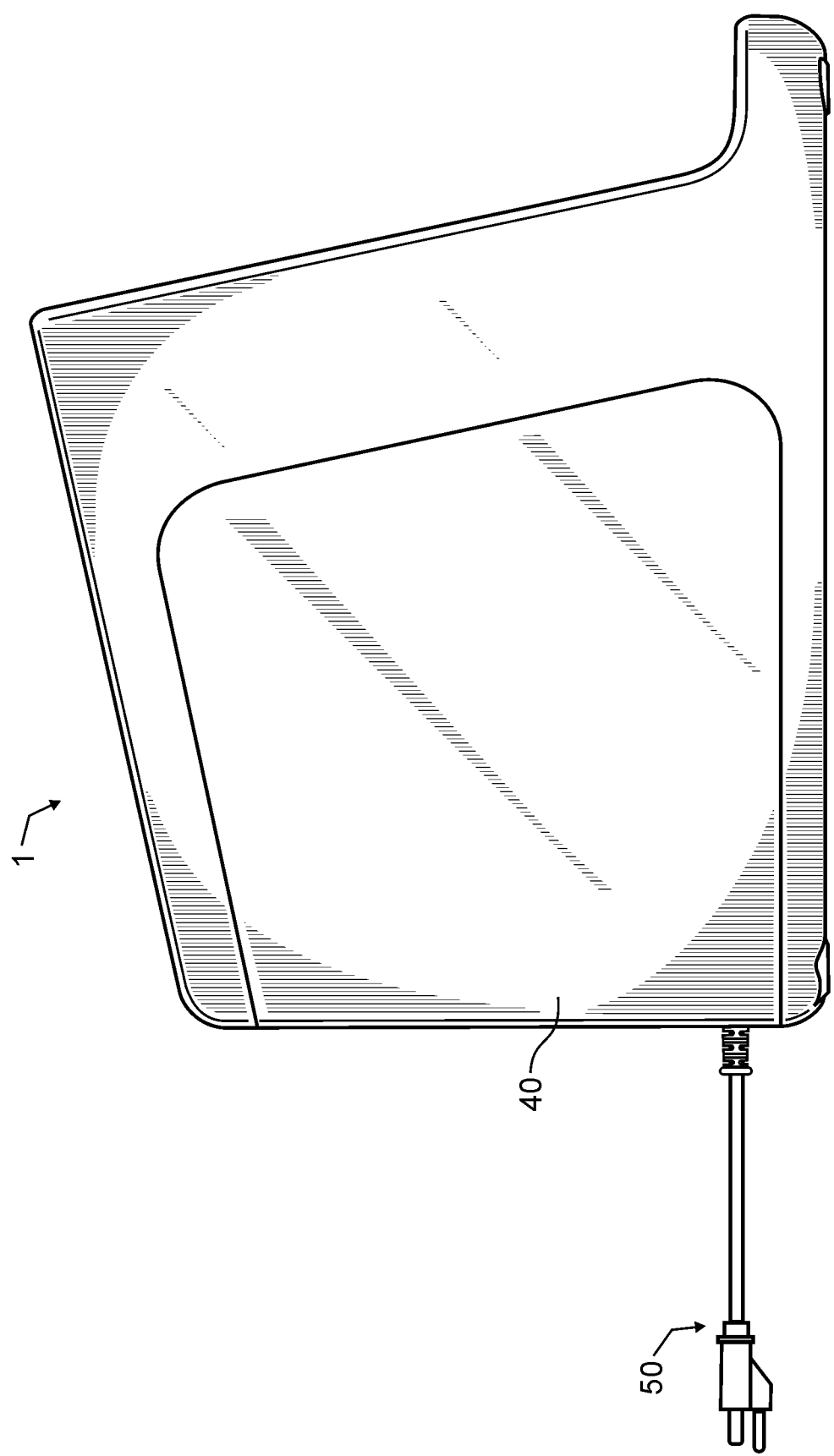

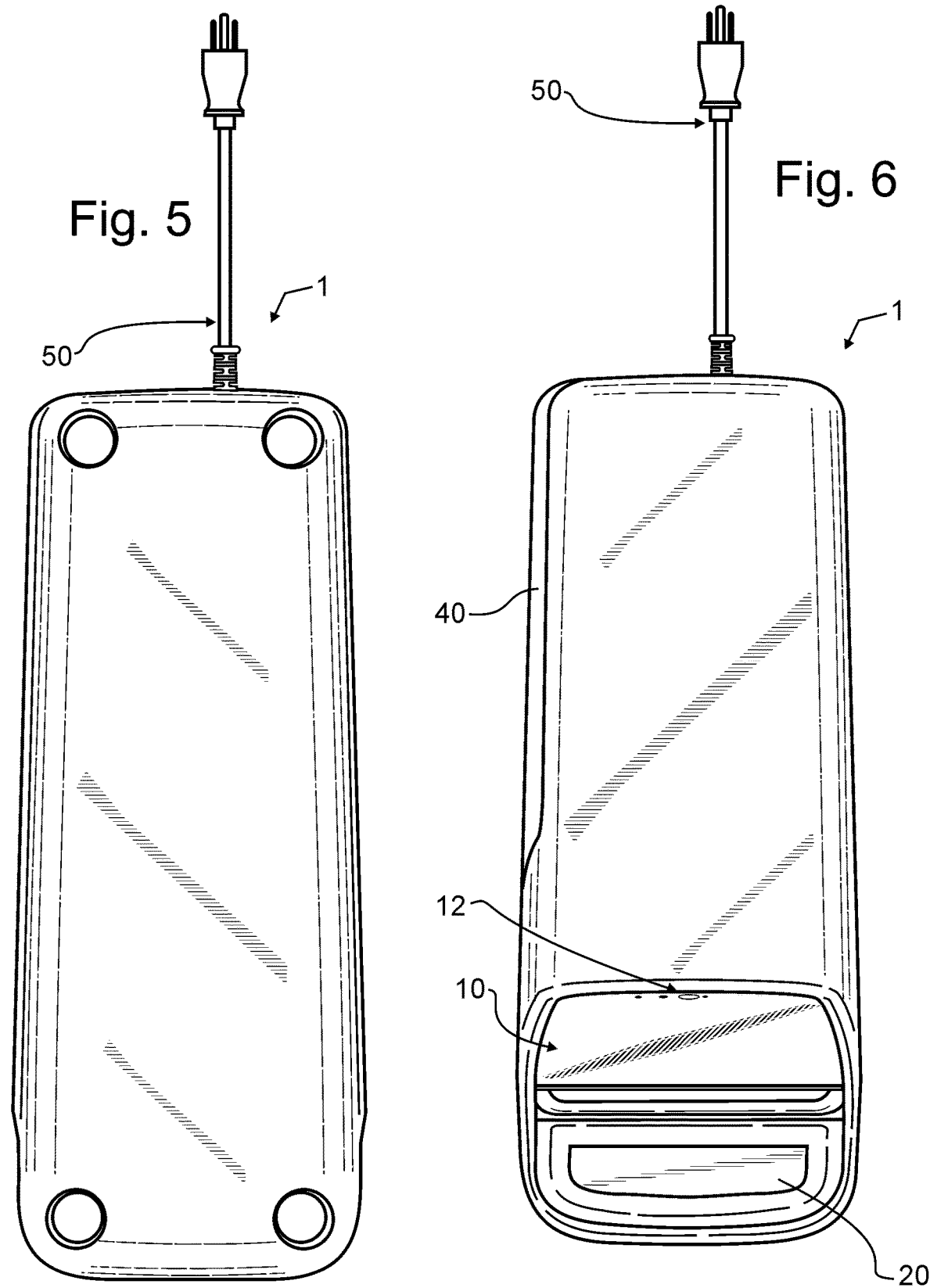

WEB ENABLED AUDIOVISUAL MEDICATION DISPENSING WITH ENHANCED COMPLIANCE VERIFICATION

BACKGROUND OF THE INVENTION

1. Field of the Invention

The present invention pertains generally to dispensers, and more particularly to an improved medication dispenser configured to dispense, validate, and record that the right person receives the right medications at the right times.

2. Description of the Related Art

A person's health is vital to their continued well-being. Recognizing this, nearly all persons in developed countries take many significant precautions every day to maintain and protect their health. One example of this is hand washing to remove dirt and potential pathogens. Most people in developed countries will wash their hands multiple times throughout the day, particularly after handling dirty or potentially contaminated objects or in advance of eating. Another example is tooth brushing and mouthwash, both aimed at preserving oral health. Yet another and very diverse example is the act of buckling a seat belt upon entering a vehicle, to protect a person in the event of emergency braking or accidents. The manufacturers of many diverse products, including but certainly not limited to soaps and disinfectants, toothpaste, toothbrushes, mouthwash, and even automobiles have worked and strived through the years to make these basic tasks that are proven beneficial to preserve people's health as easy and fast as possible, to the point where these acts become seemingly instant and automatic. When they do, there is almost no measurable burden on individuals and society to implement, and in turn the overall health of a population is greatly improved. This means for very little relative cost of time and investment, individual and societal costs such as lost work, decreased productivity, and health care costs may all be much more greatly reduced. Ultimately, these small investments provide substantial benefit to both individuals and society as a whole.

To assist in the health of individuals and societies, various researchers, scientists, engineers, and creative individuals from all walks of life, but perhaps most commonly from universities, governmental organizations, and pharmaceutical companies, have likewise created and highly refined various medication and treatment regimens. These regimens are typically targeted and specific to one particular type of disease or ailment. In many instances, these medication and treatment regimens have been so well refined that a person who would otherwise perish in very little time or suffer intolerably can instead live a long and fulfilling life. Many, many diseases that heretofore would have been completely debilitating or life-threatening have been addressed with well-conceived medication and treatment regimens.

Nevertheless, for a significant number of these regimens there are a number of inconveniences or obstacles to proper adoption by affected persons. For exemplary and non-limiting purpose, many medications require the patient to follow a fairly strict schedule. Timing can be very critical in the treatment of certain diseases, including but not limited to hypertension and diabetes.

In the exemplary case of hypertension, also known as the silent killer, a person who has missed a medicine dose may not sense or exhibit any symptoms at all. Unfortunately, the missed dose may lead to elevated blood pressure during which damage is being done that can be serious or fatal. Likewise, if the person takes too much medication in too short a time period, they may also succumb to ill affect. Also typically with mild or no symptoms but critical timing, improper diabetes medication similarly causes irreversible damage each time blood sugar levels stray too far outside of the target ranges.

Further compounding the obstacles, very commonly a person will have a plurality of medications that must be simultaneously managed. As one example, one medication may trigger an innate response within the individual a certain time thereafter, for which a second different treatment or medication may be required. One such example is in the case of some chemotherapy medicines that are beneficial but also lead to nausea. In such instances, it is common that the chemotherapy medicine is taken first, and then at a particular time interval later but in advance of the nausea setting in, an anti-nausea medication will then need to be consumed.

While timing is one requirement for the medicines to be effective, there are often other requirements as well. For example, due to some interactions with food or even with other medications, some medications may be rendered ineffective or even potentially harmful if taken in the wrong combination.

Consequently, the schedule of when to take medicines and adjuncts such as nutritional supplements in relation to meals and timing between other medications can be quite complex. As may be appreciated, and for even the most capable of persons, relying solely on memory to know when to take a set of medications, and to know that the medications have been taken, is extremely difficult. When a person is required to take a variety of medications throughout the day, each and every day for an extended period up to and often including the rest of their life, it is very easy to recall another recent medication consumption, and as a result to be unsure whether a medication was properly taken at one particular scheduled time.

Unfortunately, compliance with a prescribed medication schedule has been and still remains woefully low. According to the World Health Organization (WHO) in a 2003 report, medication non-compliance is a "worldwide problem of striking magnitude." From their data in that same report, adherence to long-term therapy for chronic illnesses in developed countries averaged 50%, and the rates were even lower in developing countries.

As already noted above with hypertension and diabetes, but applicable to many diseases and conditions, taking medications in a non-compliant manner can have very serious consequence. These consequences include a prolonging of disease, an increase in serious complications, unnecessary medical visits and emergency services, displacement to long-term care facilities, and even death. All of these adverse events of untold emotional consequence are also associated with higher medical costs and undesirable financial burden, estimated by some to be measured in the hundreds of billion dollars annually.

There are several different issues that are each independent of each other in the field of medication compliance. One is simple forgetfulness, which all persons suffer to greater or lesser degree at various times or instances. As noted above, it is very easy to mistake one recent medication consumption for another, and as a result to be unsure whether a medication was properly taken at one particular scheduled time. While this forgetfulness may impact some persons to much greater degree than others, and so in some cases may require much closer and different monitoring, there is little likelihood or chance that the patient will intentionally attempt to trick or circumvent a dispensing system. Many of the prior art systems and apparatus designed to facilitate patient compliance focus on these issues by relying on the patient to either fully manage their own medications, or at least to accurately report compliance.

A second issue arises from limitations or impairments associated with a particular patient. Impairments to sensory input, including vision, hearing, and touch, may interfere with taking medications. For exemplary and non-limiting purpose, impaired vision will interfere with proper evaluation of medication labels, potentially leading to confusion over which medication is being taken. In addition, decreased cognitive skills, physical strength, or mobility can also interfere with the taking of medications. These limitations can directly interfere with the ability of a person to access and open prescription containers or properly use various dispensers and dispensing apparatus. While the physical effects of aging, such as arthritis, failing eyesight, and poor memory are frequently associated with medication non-compliance, many other impairments that are not directly age-related can also interfere with the autonomous taking of medicines. Nevertheless, and similar to forgetfulness, these impairments do not indicate any ill intent on the part of the patient.

Another issue that arises in medication compliance is that of a patient who intentionally resists compliance. In some cases this may be due to various dementias, but in other cases may involve: adverse reactions to the medications that the patient has not shared with a physician or pharmacist; inadequate knowledge, understanding, or perception of the disease and likely treatment and non-treatment outcomes; hopelessness, frustration, or stigmatization; misunderstandings of the treatment regimen; fear of dependence; fundamental beliefs with regard to the necessity or efficacy of medications or proper diagnosis; or differing outcome goals of the patient that cause resistance to medication compliance. Unfortunately, in some of these cases the patient may attempt to circumvent a prior art dispensing system or caregiver. One example of this is the well-known "cheeking" of pills, where the patient holds the pill in their cheek, pretending to consume or swallow the pill only to remove it from their cheek when the caregiver is no longer looking. In such cases, caregivers may be trained to look into and inspect the patient's mouth immediately after the patient has allegedly consumed the medication, simply to confirm that the medication is no longer present.

Yet another issue arises when a caregiver, family member, or other person intentionally deprives the patient of a medication. This is most likely to occur when controlled or abusable narcotics, muscle relaxants, and other prescription drugs are prescribed. In many of these cases, the medications are diverted from the intended patient to another for recreational use or addict consumption. There may also still arise surprising situations where medications not otherwise expected to be diverted may in fact be. Unfortunately, such situations can become even more insidious when, due to diversion, an otherwise compliant patient is misinterpreted to be either confused, non-compliant, or drug-seeking.

To address the forgetfulness and multi-medication management components of non-compliance, over time very creative and thoughtful people have ingeniously developed pill boxes, timers, labels, and calendars to ensure that medications are taken in the appropriate schedule. Exemplary prior art pill boxes include organizing trays or compartments that require filling by a patient or caregiver. During the course of care and treatment involving many medications, treatments, and personal care products, most individuals will turn to one or more of these organizers.

Most commonly, these are multi-compartmented trays, cups, vials, or the like into which the various medications may be distributed for later consumption or application. One very common example of such an organizer is a seven compartment tray having individual flip-top lids over each compartment. The lids are labeled, typically with one or a few of the first letters of one of the seven days of the week. Consequently, a person may insert daily medicines, vitamins, and the like into each compartment. Then on Sunday they will open the dispenser labeled S, Su, or Sun, and consume each of the pills, tablets, or the like contained therein. As each new day of the week arrives, they can then open and consume or apply the contents. In the event they are not sure whether they have taken the medicines and adjuncts for the day, a simple visual inspection will allow them to correctly ascertain the status. These aids provide powerful tools to assist many patients in overcoming forgetfulness, and thereby enable them to comply with a prescribed medication schedule.

Unfortunately, these organizers only address the forgetfulness component of non-compliance, and provide no adequate way to verify that the correct medications are in the correct compartments in the correct quantities. In many cases, a patient most in need of the medication and treatment regimens will also have great difficulty self-administering effectively. In worst cases, the patient may under- or overdose one or more of the medications or treatments, which as aforementioned can also lead to detrimental or dire consequence.

In many cases, unpaid caregivers such as family members, relatives, or close friends will provide assistance to a patient for whom the requirements of a regimen, or a regimen combined with independent living, may otherwise be too great. In some cases, these caregivers may only be needed to help out with the more challenging or complex chores, which can greatly extend the ability of the patient to function independently. This is particularly effective when the assistance from the caregiver can be provided intermittently and relatively infrequently. In such cases, the medication organizers may be filled by the caregiver or by the caregiver working in harmony with the patient. Once the medication organizer is filled, and any other bigger or more complex chores are assisted with, then the patient will be able to function independently. The caregiver may then only need to call or stop by intermittently, both for social benefit and to confirm that the patient is not in immediate further need.

Unfortunately, in rare instances even the most conscientious persons, not limited to caregivers but also including pharmacists, will accidentally improperly fill dispensers or prescriptions. Further, and again in rare instances, a physician may accidentally prescribe medications that might be incompatible with each other or a patient may be under the care of multiple physicians who are not aware of all of the medications prescribed by other physicians. While pharmacists may catch many of these mistakes, the old adage "to err is human" is applicable.

Other more automated systems and apparatuses provide pill extraction from separate bins, or from blister packs by pressing the pills out of the individual compartments. These systems and apparatuses offer benefit in the ability to adjust a medication regimen nearly instantaneously, and can be used with a wide range of both medications and adjuncts, as well as on-demand usage where permitted by a prescribing physician or by the nature of the drug or adjunct. However, in exchange for this flexibility these systems tend to be very complex, expensive, and yet not free from serious risk.

When these pill extraction systems and apparatuses malfunction, they require immediate replacement or they are very disruptive to the care system in place for a particular patient. Unfortunately, a relatively minor malfunction might not be easily identified or detected and yet can lead to a very serious patient overdose or missed dose(s). The malfunction, for very simplified exemplary and non-limiting purposes, might be a mechanical jam or similar malfunction that results in only one particular medication not being dispensed. In such case, and particularly where many other medications are being successfully dispensed, the malfunction might not be discovered until the next fill cycle. The patient could unintentionally be on a medication holiday with regard to a critical medication for weeks. Even when functioning perfectly, in many cases these apparatuses cannot readily accommodate a patient traveling for even a part of a day without requiring substantial adaptation on the part of the patient and total loss of many of the benefits otherwise offered by the apparatus and system.

A large number of patents and published applications exemplary of the aforementioned prior art, each individual one of varying relevance with the relevant teachings and contents incorporated herein by reference, include: 3,732,544 by Obland, entitled "Computer-controlled article merchandising system for prescription drugs and like articles"; 4,360,125 by Martindale et al, entitled "Medication inventory device"; 4,616,316 by Hanpeter et al, entitled "Medication compliance monitoring device having conductive races upon a frangible backing of a medication compartment"; 4,653,009 by Brown, entitled "Stamp dispenser"; 4,695,954 by Rose et al, entitled "Modular medication dispensing system and apparatus utilizing portable memory device"; 5,408,443 by Weinberger, entitled "Programmable medication dispensing system"; 5,630,347 by Elvio, entitled "Pharmaceutical dispenser for dispensing a variable and predetermined number of tablets or similar products packaged in a blister band"; 5,713,485 by Liff et al, entitled "Drug dispensing system"; 6,004,020 by Bartur, entitled "Medication dispensing and monitoring system"; 6,263,259 by Bartur, entitled "Medication dispensing and monitoring system"; 6,415,202 by Halfacre, entitled "Tamper resistant programmable medicine dispenser"; 6,529,801 by Rosenblum, entitled "Automatic prescription drug dispenser"; 6,594,549 by Siegel, entitled "Web-enabled medication dispenser"; 6,607,094 by MacDonald, entitled "Apparatus and method for dispensing medication"; 6,615,107 by Hubicki, entitled "Automated system and method for dispensing medications for low visions elderly and blind individuals"; 6,625,518 by Depeursinge, entitled "Method supporting administration of a prescribed drug and implementing said method"; 6,697,704 by Rosenblum, entitled "Automatic prescription drug dispenser"; 6,732,884 by Topliffe et al, entitled "Bulk medication dispenser and monitoring device"; 6,766,218 by Rosenblum, entitled "Automatic prescription drug dispenser"; 6,957,126 by Kim, entitled "Tablet cassette control method of medication dispensing and packaging system"; 6,961,285 by Niemiec et al, entitled "Drug delivery management system"; 7,155,202 by Helal, entitled "Portable device medical assistant"; 7,359,765 by Varvarelis et al, entitled "Electronic pill dispenser"; 7,369,919 by Vonk et al, entitled "Medication adherence system"; 7,440,817 by Fu, entitled "Method and control unit for medication administering devices"; 7,711,449 by Abdulhay et al, entitled "Personal medication dispenser"; 7,801,745 by Walker et al, entitled "Methods and apparatus for increasing and/or monitoring a party's compliance with a schedule for taking medicines"; 7,873,435 by Yuyama et al, entitled "Dispensing support device and dispensing support method"; 7,917,246 by Handfield et al, entitled "Lockable medication dispensing apparatus with authentication mechanism"; 7,946,448 by Madey, entitled "Pill dispenser"; 7,991,507 by Liff et al, entitled "Method for controlling a drug dispensing system"; 8,019,471 by Bogash et al, entitled "Integrated, non-sequential, remote medication management and compliance system"; 8,175,746 by Godlewski, entitled "Weight based dispensing system"; 8,224,483 by Ansari et al, entitled "System for checking the accuracy of a prescription fill"; 8,600,548 by Bossi et al, entitled "Remote medication management system"; 8,600,549 by Park, entitled "Automatic drug dispensing and dosing time reminder device"; 9,836,583 by Garcia et al, entitled "Automated medication adherence system"; 10,279,985 by Mills et al, entitled "Machine and methods for dispensing nutritional supplements and multi-serving cartridge therefor"; 10,327,995 by Wang et al, entitled "Automatic medicine retrieving device"; 10,343,806 by Fagen et al, entitled "Mechanism for dispensing pills from an array-type package"; Des. 459,987 by Christianson, entitled "Pill dispenser"; Des. 555,893 by Mulaw, entitled "Medication organizer"; Des. 773,175 by Fagen, entitled "Medication dispenser"; Des. 812,246 by Hommel et al, entitled "Dispenser"; Des. 828,013 by Van Wijngaarden et al, entitled "Pill canister"; 2001/0054071 by Loeb, entitled "Audio/Video conference system for electronic caregiving"; 2002/0113077 by Topliffe et al, entitled "Bulk medication dispenser and monitoring device"; 2002/0153411 by Wan et al, entitled "Online medicine cabinet"; 2005/0259641 by Beninato et al, entitled "Systems and methods for communication platforms"; 2006/0161295 by Yun, entitled "Telemedic monitoring system"; 2006/0184271 by Loveless, entitled "Cartridge loaded automatic prescription pill dispensing system and dispensing unit and cartridge for use therein"; 2006/0276931 by Walker et al, entitled "Systems and methods for improved health care compliance"; 2008/0105588 by Tran et al, entitled "Systems and method for monitoring pill taking"; 2009/0022293 by Routt, entitled "Telecommunications system for monitoring and for enabling a communication chain between care givers and benefactors and for providing alert notification to designated recipients"; 2009/0105876 by Simpson et al, entitled "Pill dispensing apparatus"; 2009/0315702 by Cohen Alloro et al, entitled "Medication dispenser"; 2010/0026817 by Ryan et al, entitled "Medical video communication systems and methods"; 2010/0076595 by Nguyen, entitled "Smart pill dispenser"; 2010/0152885 by Regan et al, entitled "Automated diagnostic kiosk for diagnosing diseases"; 2010/0164716 by Estevez et al, entitled "System and method for monitoring dispensing of medication"; 2010/0194976 by Smith et al, entitled "Computer based aids for independent living and health"; 2010/0256808 by Hui, entitled "Method and apparatus for dispensing medicine"; 2011/0115875 by Sadwick et al, entitled "Assisted communication system"; 2011/0202174 by Bogash et al, entitled "Integrated non sequential remote medication management and compliance system"; 2012/0101630 by Daya et al, entitled "Pharmaceutical packing and method for delivery of same"; 2014/0309769 by Wu et a, entitled "Automatic pill dispenser with water heater"; 2016/0001955 by Wang et al, entitled "Pill dispenser and system"; and 2018/0029779 by Go, entitled "Pill box in automatic pill dispenser".

Another alternative medication compliance approach has been for a pharmacy to aggregate and insert combinations of medications into sequential sealed pouches, with each pouch corresponding to a day and time that the aggregated medications should be taken. A single dose may comprise a single pouch, or in some instances may comprise several pouches. Each pouch may for exemplary purpose have a clear side allowing view of the medications and a translucent or opaque side that includes indica displaying the date, time and patient. Such indicia may be in the form of human-readable text, machine readable codes or identification such as barcodes, or both. These pouches may in some cases simply be stacked in sequential order. However, much more commonly they are either rolled into a "coil" similar to a coiled clock spring or alternatively stacked in a back and forth manner commonly referred to as a "z" configuration or concertina fold. A patient needs only check the indicia on the sealed pouch, confirm that the contents are for the patient, and confirm that the timing is right before consuming the medications.

These aggregated medication pouches may be manually or automatically dispensed. Exemplary aggregated medication pouch dispensers, the relevant teachings and contents which are incorporated herein by reference, include: 5,945,651 by Chorosinski et al, entitled "Remotely programmable medication dispensing system"; 6,394,306 by Pawlo et al, entitled "Medication dispenser for dispensing flat dosage forms"; 6,527,138 by Pawlo et al, entitled "Medication dispenser for dispensing flat dosage forms"; 7,264,136 by Willoughby et al, entitled "Medication dispensing Method and apparatus"; 7,963,201 by Willoughby et al, entitled "Medication dispensing method and apparatus"; 8,196,774 by Clarke et al, entitled "Remote pharmaceutical dispensing"; 8,453,874 by Simpson et al, entitled "Pill dispensing apparatus"; 8,757,435 by Van Oort et al, entitled "Method, system and device for assisting a patient complying with a medical regime"; 2011/0068115 by Choi et al, entitled "Medication supporting apparatus and method"; 2012/0083666 by Waugh et al, entitled "Medication delivery and compliance system method and apparatus"; 2012/0081225 by Waugh et al, entitled "Medication delivering and validation system, method and apparatus"; and 2014/0005826 by Apell et al, entitled "Method for monitoring the filling of a medication dispenser, and medication dispenser".

In 5,945,651 by Chorosinski et al, two pairs of main drive rollers feed the aggregated medication pouches past a barcode reader. The barcode reader reads the barcode information present on the aggregated medication pouches. Subsequently, the "tape" passes through a guillotine cutter that severs the tape to dispense the medication pouch.

Similar apparatuses are illustrated in the Willoughby et al U.S. Pat. Nos. 7,264,136 and 7,963,201, but instead of a guillotine cutter the two pairs of main drive rollers turn at different rates, to stretch and thereby sever a perforated divider between adjacent medication pouches. The Willoughby et al patents also discuss using an Optical Character Recognition (OCR) device as an alternative to an optical bar code scanner. These patents also disclose the use of either a continuous string or tape of aggregated medication pouches or a plurality of discrete single packages that are stacked in proper order.

While the pouches are pre-packaged in some quantity in advance, meaning a change to the medication can disrupt a certain number of already packaged pouches, in return they offer greater convenience and safety for the patient since the patient is only required to check the printing on each package to validate that the medications are for them and to know when to consume the contents of the next pouch.

Some of the dispensing apparatuses allow a patient to dispense aggregated medications in advance. This allows the patient to pack medications required during a day trip or even a multi-day trip. As a result, they can travel without the dispenser without any consequential change in their routine, and still benefit from the convenience and safety of the pouches.

Many of these very creative prior art dispensers facilitate delivery of a variety of medications quickly and efficiently. However, and as noted above, without additional compliance verification a dispenser provides only very nominal verification that the right person actually received the medicine at the right time. Most systems and apparatuses rely entirely upon the patient to confirm that the medications have in fact been taken. Some validate this by checking the container to ensure a dose was removed, but again without verifying that the medication was actually consumed or by whom. While this approach is quite effective for ordinary patients of sound mind and reason who wish to comply, moments or periods of stress or dementia in some patients will still lead to non-compliance.

In such cases, a caregiver such as a home health aid, family member, neighbor, or close friend can still be of great benefit to the patient. In such instances where a suitable caregiver is available, the caregiver can check on the patient in person at the right time intervals to ensure that the patient is actually complying with the medication regimen. Simple patient confirmation that a medication has been taken my then be confirmed by the caregiver, and compliance is augmented by the caregiver reinforcing timing requirements.

Unfortunately, many of these regimens require that the medication be taken multiple times throughout the day. This means the caregiver should be present for each requisite time, making this monitoring time consuming and difficult for caregiver. As a result, caregivers often experience mental, physical, and financial stress trying to assist a patient in need. As dedicated and selfless as these individuals may be, rarely can they always provide the desired level of care needed to ensure medication compliance. These issues are only further compounded when a patient intentionally chooses to not comply, or when an unscrupulous caregiver mistreats a patient and forces the patient to not comply such as in the diversion of prescriptions. In such instances, the simple patient confirmation that a medication has been taken fails to adequately address patient compliance.

To address these concerns, and particularly with high risk medications and high risk patients, some providers will require the individual to receive the medication from a nurse or other licensed health care provider. In such situations, this may force the patient out of an independent or assisted living situation into a long-term care facility.

One approach to overcoming these weaknesses in compliance verification comprises the inclusion of cameras that may take photographs or videos of the person accessing the medication dispenser. Exemplary patents, the relevant teachings and contents which are incorporated by reference herein, include: 5,646,912 by Cousin, entitled "Medication compliance, co-ordination and dispensing system"; 6,539,281 by Wan et al, entitled "Online medicine cabinet"; 8,060,249 by Bear et al, entitled "Medication dispenser with integrated monitoring system"; 2016/0283691 by Ali, entitled "System, method and container assembly for prevention of drug diversion and for compliance assurance"; and 2017/0076061 by Axelrod et al, entitled "Monitoring system for medication compliance". 5,646,912 by Cousin describes a mini camera snapping a picture of the patient removing the pill from the dispenser, or, in an alternative embodiment, a video recorder recording and/or transmitting live pictures for a predetermined length of time after the pill is removed. In 6,539,281 by Wan et al, when a user stands in front of the medicine cabinet, a video camera in conjunction with face recognition software identifies the user. In addition, at least one sensor reads the medication label, and a weight sensor determines the amount of medication. In addition, if instructed by the user or based on other criteria, the medicine cabinet can initiate a video conference with the doctor or other health provider. 2017/0076061 by Axelrod et al describes an add-on motion-activated camera to a prior art prepackaged pouch dispenser that takes video of the medication pouch indicia, the user, and records the date and time.

While certainly a significant improvement over simple button presses, these improved video validation systems still suffer from easy manipulation by reluctant patients and by drug diverters. In consideration thereof, a number of additional systems have been devised that offer even better compliance verification.

One approach to this has been illustrated by Guan, Hanina, and Kessler in a number of US patents, the relevant teachings and content incorporated herein by reference, including: 8,731,961 by Hanina et al, entitled "Method and apparatus for verification of clinical trial adherence"; 8,781,856 by Hanina et al, entitled "Method and apparatus for verification of medication administration adherence"; 9,256,776 by Hanina et al, entitled "Method and apparatus for identification"; 9,293,060 by Hanina et al, entitled "Apparatus and method for recognition of patient activities when obtaining protocol adherence data"; 9,665,767 by Guan et al, entitled "Method and apparatus for pattern tracking"; 9,679,113 by Hanina et al, entitled "Medication adherence monitoring system and method"; 9,875,666 by Hanina et al, entitled "Apparatus and method for recognition of patient activities"; 10,116,903 by Hanina et al, entitled "Apparatus and method for recognition of suspicious activities"; and 10,558,845 by Guan et al, entitled "Apparatus and method for determination of medication location". In these patents, medication compliance is determined using a single camera and predetermined movements, referred to as "gestures," that are determined to be highly indicative of a person grasping and subsequently consuming the medication. The gestures are confirmed using gesture recognition software. If not automatically recognized, then the gestures still may be confirmed subsequently through human review and analysis. While this approach again offers substantial improvement over the prior art in reliability and automation, the method and apparatuses are dependent upon the patient complying with the required movements and motions. The patient must be capable of closely following the motion or gesture to permit reliable automated identification and confirmation. Even very capable persons will occasionally forget or otherwise deviate from the intended motion, as evidenced by our less than perfect bowling, batting, tennis, and golf swings. Consequently, this approach may work very well with many patients, but still leaves the apparatus inapplicable to patients with limitations, and also undesirably susceptible to either intentional or inadvertent manipulation of the dispensing system.

In addition to confirming medication compliance, and as noted herein above, confirming that the proper medication for the patient has actually been dispensed is also beneficial. In doing so, potential errors incurred during filling of the dispenser or from the pharmacy or prescribing physician(s) may be caught and the likelihood of harm greatly diminished. The Wan et al '281 patent discussed herein above achieves this by not only using photographic or video record of the patient to confirm patient identification, but also by reading medication containers. Unfortunately, this does not verify the actual contents of the medication containers, meaning the containers could be tampered with, altered, or improperly originally filled.

To better reduce the likelihood of prescription or fill errors or intentional diversion, while still providing patient verification, the Bear et al '249 patent incorporated by reference herein above describes an image capturing device focused on the interior space of a storage compartment in a dispenser device. The image capturing device is part of the system to provide verification that appropriate medications have been loaded in the dispenser, removed from the dispenser, and/or remain loaded in the dispenser. A user identification module is described as being structured to detect a fingerprint, biometric shape of a user's hand or finger, retinal scan profile, or voice recognition to identify a proper user.

Similarly, in U.S. Pat. No. 8,538,775 by Skomra, entitled "Mobile wireless medication management system", the relevant teachings and contents which are incorporated herein by reference, a patient, medication provider, medication, correct dosage, and correct timing are each identified and authenticated with images, and the medication provider is allowed to either confirm or reject use of the medication by the patient.

A number of the Guan, Hanina, and Kessler patents incorporated by reference herein above discuss requiring the patient to display the medication to the camera for identification as a part of the gestures, specifically including 8,731,961; 8,781,856; 9,293,060; 9,679,113; 9,875,666; and 10,116,903. In addition, in U.S. Pat. No. 9,824,297 by Guan et al, entitled "Method and apparatus for medication identification," the teachings and content which are incorporated herein by reference, an improved method and technique for identifying the medication is described.

Kamen et al in U.S. Pat. No. 9,400,873, entitled "System, method, and apparatus for dispensing oral medications", and subsequent continuation patents and published applications 9,465,919; 10,185,812; 10,468,132; and 2020/0066388; each entitled "Pill dispenser," the relevant teachings and contents of each which are incorporated by reference herein, each describe at least a first camera used to identify and confirm presence of an intended medication dose. The same at least first camera is subsequently used to confirm that the intended medication dose has been removed from the dispenser. A different camera is used to capture the user of the apparatus, which in some instances is the patient. Unfortunately, there is no direct confirmation that the patient is the person who in fact removed the medication dose from the apparatus, nor that the patient is actually taking the medication that was confirmed to be in the dispenser. In other words, the Kamen et al apparatus may be tricked by movements occurring between the field of view of the two cameras. This limitation creates an opportunity for an unscrupulous person to deprive a patient who may be in great need of the medication.

Recognizing previous limitations, one of the present inventors has heretofore obtained a number of patents commonly owned with the present invention, each incorporating very beneficial apparatuses and methods that are also relevant to the present invention. These US patents and published applications, the teachings and contents which are incorporated herein by reference, include: 9,202,011 by Lavin, entitled "Web enabled audiovisual medication dispensing"; 10,078,732 by Lavin, entitled "Web enabled audiovisual medication dispensing"; 10,347,377 by Lavin, entitled "Web enabled audiovisual medication dispensing"; 2012/0323360 by Lavin, entitled "Web enabled audiovisual medication dispensing"; and 2016/0055318 by Lavin, entitled "Web enabled audiovisual medication dispensing".

Additional patents of somewhat less relevance, the relevant teachings and contents which are also incorporated herein by reference, include: 7,654,230 by Kroll, entitled "Domestic animal telephone"; 7,878,152 by Kroll, entitled "Domestic animal telephone"; 8,201,522 by Kroll, entitled "Domestic animal telephone"; 2011/0080459 by Kroll, entitled "Domestic animal telephone"; and Des. 699,758 by Lavin et al, entitled "Pet communication device".

In addition to the foregoing patents, Webster's New Universal Unabridged Dictionary, Second Edition copyright 1983, is incorporated herein by reference in entirety for the definitions of words and terms used herein.

As may be apparent, there are significant challenges associated with dispensing medications to patients that either are significantly challenged in the use of modern dispenser technologies, resist complying, or who are vulnerable to diversion of medication. Diversion, as noted herein above, can lead to both emotional and physical harm to a patient in need of the medications. Even individuals not otherwise ordinarily prone will undesirably be tempted when a dispensing apparatus presents clear opportunities for diverting the medications. In spite of the enormous advancements and substantial research and development that has been conducted, there still remains a need for medical care devices for delivery of medication to these patients that may allow the patients to remain in their homes longer, reduce costs of medical care, and provide a way for caregivers to remotely ensure the delivery of the correct type and quantity of medications to their charges.

SUMMARY OF THE INVENTION

In a first manifestation, the invention is a web enabled audiovisual medication system with enhanced compliance verification, comprising in combination a web enabled audiovisual medication dispenser and a remote caregiver apparatus. The remote caregiver apparatus has a microphone configured to capture audio input and transmit the audio input to the web enabled audiovisual medication dispenser. A speaker is configured to receive an audio signal originating at the web enabled audiovisual medication dispenser and reproduce an audible output. A camera is configured to capture images of a caregiver and transmit the images to the web enabled audiovisual medication dispenser. A display screen is configured to receive a video signal originating at the web enabled audiovisual medication dispenser and produce a visual display. The web enabled audiovisual medication dispenser has a housing; web link circuitry configured to establish audiovisual communication with the remote caregiver device; a microphone electrically coupled to the web link circuitry and configured to capture audio input and transmit the audio input to the web link circuitry, and the web link circuitry configured to receive the audio input and transmit the audio input to a caregiver; a speaker electrically coupled to the web link circuitry and configured to receive an audio signal originating at the remote caregiver apparatus from the web link circuitry and reproduce an audible output; and a display screen electrically coupled to the web link circuitry and configured to receive a video signal originating at the remote caregiver apparatus from the web link circuitry and produce a visual display. A medication pouch chamber is enclosed within the housing. A plurality of medication pouches are stored within the medication pouch chamber that each contain at least one medication. A medication pouch receptacle is partially enclosed within the housing and configured to receive and hold at least one of the plurality of medication pouches. A dispenser is configured to transfer the at least one of the plurality of medication pouches stored within the medication pouch chamber from the medication pouch chamber to the medication pouch receptacle. A first imaging apparatus generates an image of the medication pouch receptacle and is configured to capture a medication pouch receptacle image of the medication pouch within the medication pouch receptacle and communicate the medication pouch receptacle image through the web link circuitry to the remote caregiver apparatus and is further configured to capture a medication pouch removal image of at least a portion of a patient's hand during the patient's removal of the medication pouch from the medication pouch receptacle. A second imaging apparatus has a functional field of view that includes at least a patient's hand, arm, and face and further includes a medication handling region extending substantially between the patient's face to at least adjacent to the medication pouch receptacle. The second imaging apparatus is configured to capture a first medication handling region image of the patient, and a second medication handling region image of the patient removing at least one medication from the at least one of the plurality of aggregated medication pouches, and a third medication handling region image of the patient consuming the at least one medication removed from the at least one of the plurality of aggregated medication pouches.

In a second manifestation, the invention is an audiovisual medication dispenser with enhanced compliance verification. The audiovisual medication dispenser has a housing. A medication chamber is enclosed within the housing, and a plurality of medications are stored within the medication chamber. A medication receptacle is partially enclosed within the housing and configured to receive and hold at least one of the plurality of medications. A dispenser is configured to transfer the at least one of the plurality of medications stored within the medication chamber from the medication chamber to the medication receptacle. A first imaging apparatus generates an image of the medication receptacle and is configured to capture a medication receptacle image of the medication within the medication receptacle and is further configured to capture a medication removal image of at least a portion of a patient's hand during the patient's removal of the medication from the medication receptacle. A second imaging apparatus has a functional field of view including at least a patient's hand, arm, and face and further includes a medication handling region extending substantially between the patient's face to at least adjacent to the medication receptacle. The second imaging apparatus is configured to capture a first medication handling region image of the patient, and a second medication handling region image of the patient consuming the at least one medication removed from the medication receptacle.

In a third manifestation, the invention is a method of validating and documenting that a patient has received medications prescribed to the patient within a prescribed time window. The method includes the steps of: inserting at least one medication into at least one aggregated medication pouch; securely storing the at least one aggregated medication pouch within a medication pouch chamber located and fully enclosed within a medication dispenser housing; transferring the at least one aggregated medication pouch from the medication pouch storage chamber to an externally accessible medication pouch receptacle that is configured to receive and retain the at least one aggregated medication pouch and expose the at least one aggregated medication pouch to manual access; generating a first video image having a field of view substantially consumed by the medication pouch receptacle; and generating a second video image synchronous in time with the first video image and having a field of view including at least a patient's hands, arms, and face and further including a medication handling region extending substantially between the patient's face to at least adjacent to the medication pouch receptacle. The first and second video images capture the patient removing the at least one aggregated medication pouch from the medication pouch receptacle and subsequently capture the patient removing and consuming the at least one medication from the at least one aggregated medication pouch.

OBJECTS OF THE INVENTION

Exemplary embodiments of the present invention solve inadequacies of the prior art by providing: a locked and particularly tamper resistant housing; timers and alarms; a receptacle for aggregated medication pouches; a cutter configured to separate one or more of the aggregated medication pouches from a ribbon or strip originally containing many such pouches, the cutter also configured to notch a pouch to facilitate opening by a patient, and further configured to form a part of the tamper resistance; a medication pouch receptacle configured to receive the one or more aggregated medication pouches cut from the strip; at least a first imaging apparatus displaying the medication pouch receptacle and configured to communicate the image at least to a remote apparatus for compliance; and a second imaging apparatus displaying at least adjacent to the medication pouch receptacle and configured to capture an image of the patient handling and taking the medication from the pouch and configured to communicate the image at least to a remote apparatus for compliance.

The present invention and the preferred and alternative embodiments have been developed with a number of objectives in mind. While not all of these objectives are found in every embodiment, these objectives nevertheless provide a sense of the general intent and the many possible benefits that are available from embodiments of the present invention.

A first and overarching object of the invention is to provide a medication dispenser configured to dispense, validate, and record that the right person receives the right medications at the right times. As a corollary thereto, an object of the invention is to reduce the chance for medication errors. As a further corollary thereto, an object of the invention is to provide easy medication loading, with multi-stage validation of medications prior to consumption. As yet another corollary thereto, an object of the invention is to confirm current prescription information, and validate individual medications being dispensed. As another corollary, an object of the invention is to confirm compatibility of various medications being dispensed, including not only whether there are any known drug contraindications but also whether individual medications may be taken together, e.g. if one medication is to be taken with food and another without. As yet a further corollary, an object of the invention is to identify and validate the identity of the patient receiving the medication being dispensed.

An additional object of the present invention is to enable improved remote monitoring and assistance by caregivers. As a corollary thereto, an object of the invention is to provide a medication dispenser with selective automated or caregiver-controlled medication dispensation. As a further corollary where appropriate, an object of the invention is to identify and validate the identity of a caregiver.

Another object of the invention is to improve patient compliance with medication consumption. As a corollary thereto, an object of the invention is to alert the patient when it is time to take medications such as with an alarm or other technique. As another corollary thereto, an object of the invention is to record and store images validating the medications being taken, and the patient taking the medication through substantially the full movement from the medication pouch basin to the patient's mouth and the subsequent swallowing thereof, thereby providing automated creation of a reliable and readily validated compliance log. As a further corollary thereto, an object of the invention is to provide dispensation of medications with greatly diminished chance of damaging individual medications. As an additional corollary thereto, an object of the invention is to assist with effective patient compliance not only at home but also when a patient is traveling away from home.

A further object of the invention is to provide physical security to the dispenser, to reduce the likelihood of medication diversion and to reduce the likelihood of a patient removing and consuming excess medications from within the dispenser.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which:

FIG. 4 illustrates the preferred embodiment web enabled audiovisual medication dispensing apparatus with enhanced compliance verification of FIG. 1 from a left side elevational view.

FIG. 5 illustrates the preferred embodiment web enabled audiovisual medication dispensing apparatus with enhanced compliance verification of FIG. 1 from a bottom plan view.

FIG. 6 illustrates the preferred embodiment web enabled audiovisual medication dispensing apparatus with enhanced compliance verification of FIG. 1 from a top plan view.

DESCRIPTION OF THE PREFERRED EMBODIMENT

Figure 1:
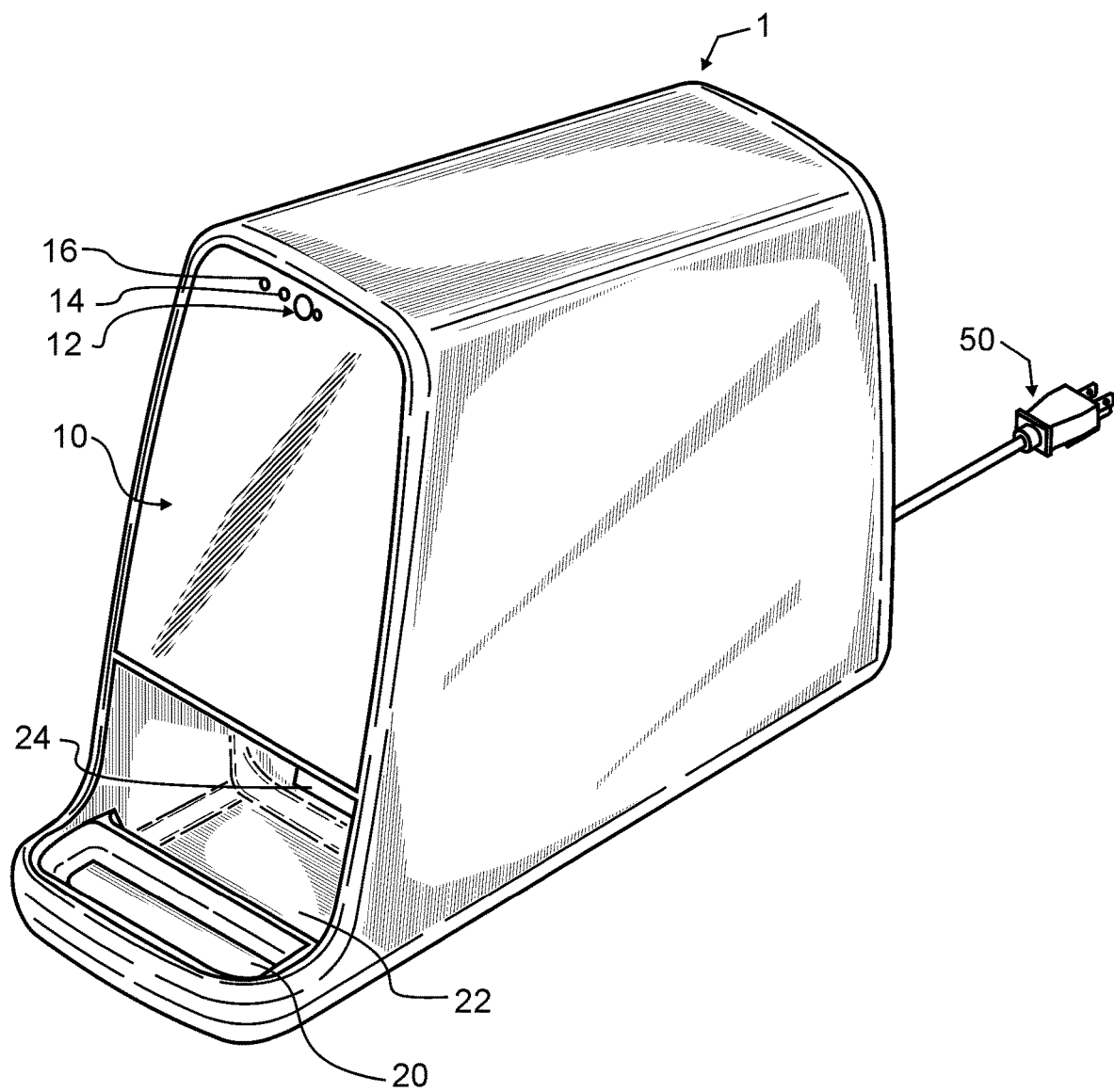
FIG. 1 illustrates a preferred embodiment web enabled audiovisual medication dispensing apparatus with enhanced compliance verification designed in accord with the teachings of the present invention from an isometric view.
Figure 2:
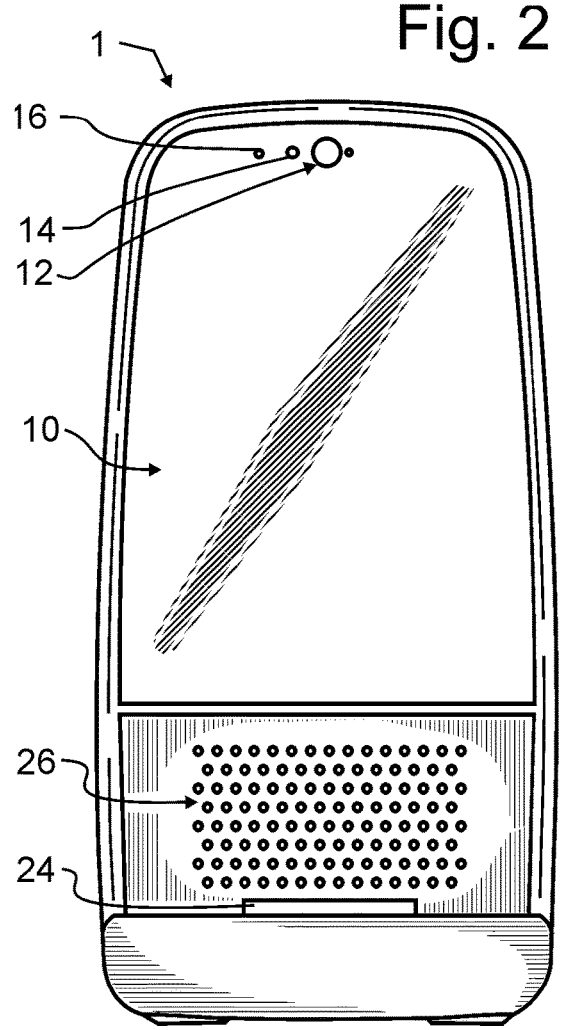
FIG. 2 illustrates the preferred embodiment web enabled audiovisual medication dispensing apparatus with enhanced compliance verification of FIG. 1 from a front elevational view.

Manifested in the preferred embodiment, the present invention provides a medication dispenser configured to dispense, validate, and record that the right person receives the right medications at the right times. FIGS. 1-6 illustrate preferred embodiment medication dispenser 1 from various external views. As best visible in FIG. 1, preferred embodiment medication dispenser 1 has a touch video display 10 with built-in components including front camera 12, microphone 14, and indicator light 16. Medication packets are dispensed through medication door 24 into a medication pouch basin 22. From medication pouch basin 22, patients may either open a dispensed packet and place the individual pills in medication basin 20 prior to consumption, or take the medication packet and directly ingest the contents. The geometry of medication basin 20 and medication pouch basin 22 may vary from the open-top receptacles illustrated, but will be understood herein to be suitable receptacles for discrete medications and medication pouches, respectively.

As evident from the Figures, medication pouch basin 22 is primarily enclosed within right housing portion 30 and left housing portion 34, but has an opening to the exterior of preferred embodiment medication dispenser 1. This opening into medication pouch basin 22 is hand accessible, and most preferably only accessible from a single general direction.

Figure 3:
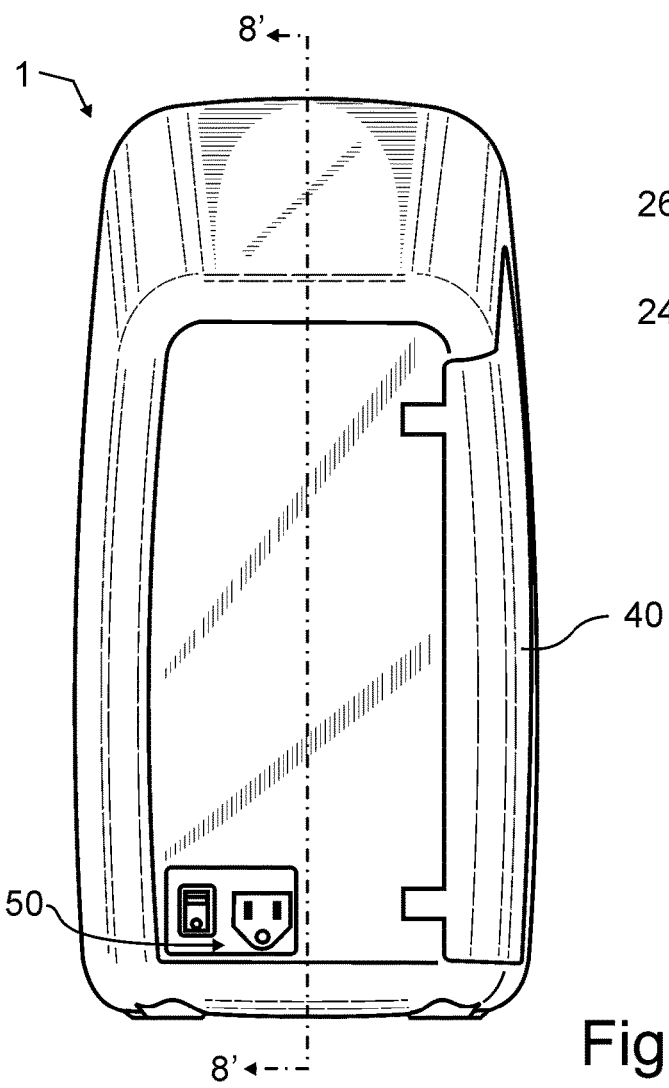
FIG. 3 illustrates the preferred embodiment web enabled audiovisual medication dispensing apparatus with enhanced compliance verification of FIG. 1 from a rear elevational view.

As best visible in FIGS. 3, 4, and 6, medication dispenser 1 also has a medication door 40 which is normally locked, but can be unlocked for exemplary and non-limiting purpose at the pharmacy to allow for the medication packets to be loaded into the medication dispenser 1 through medication door 40. One or more locks such as locks 42, 43 further described herein below may be actuated by one or more of a key, electronic key, biometric data, or remote activation to allow access to medication pouch spool chamber 35 and an aggregated medication pouch spool located therein. In embodiments that enable locks 42, 43 to be activated electrically or electronically, and in the event service is required, the locks may be activated according to a suitable protocol that may include actuation by any remote monitor such as a pharmacy, service center, remote caregiver, or any other suitably authorized party.

To power medication dispenser 1, a power plug 50 is provided. However, internal batteries, an Uninterruptible Power Supply (UPS), or other suitable power sources may also be used to power or act as suitable power back up in the event of a power line failure.

Figure 7:
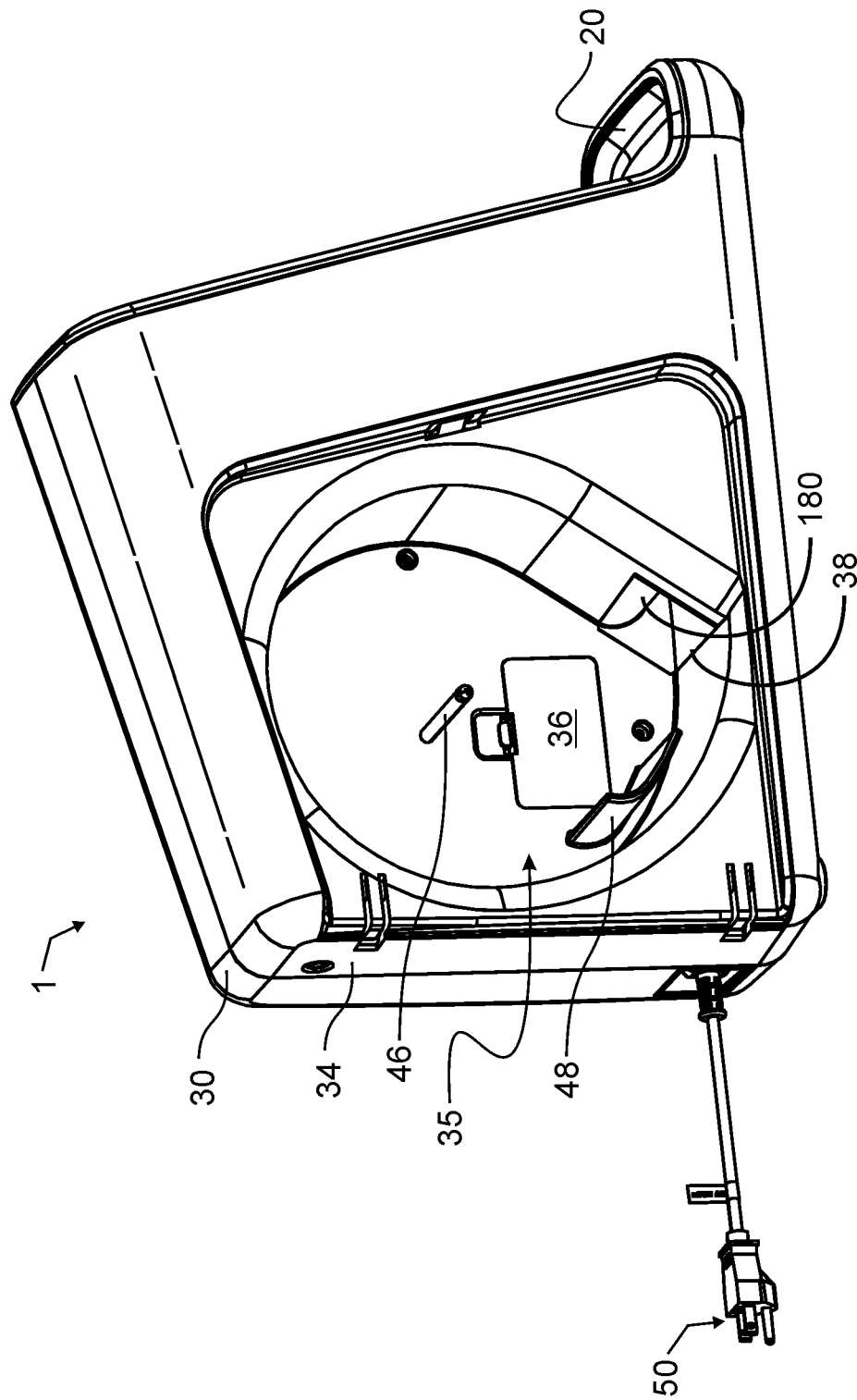
FIG. 7 illustrates the preferred embodiment web enabled audiovisual medication dispensing apparatus with enhanced compliance verification of FIG. 1 from a left and rear projected view, with the medication door removed to reveal the medication spindle and medication roll guides.
Figure 8:
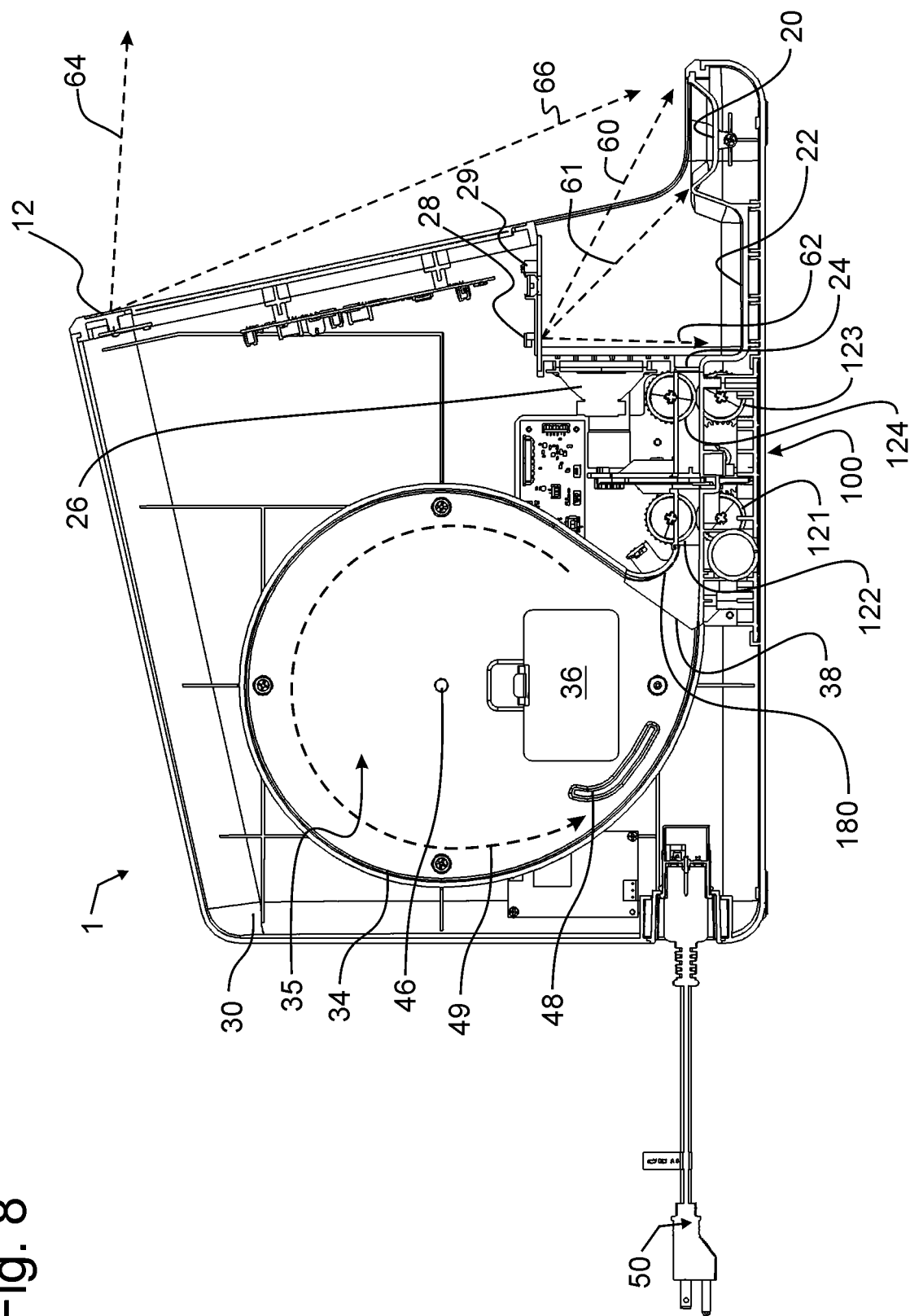
FIG. 8 illustrates the preferred embodiment web enabled audiovisual medication dispensing apparatus with enhanced compliance verification of FIG. 1 from a sectioned side elevational view sectioned along line 8' in FIG. 3.

FIG. 7 illustrates preferred embodiment medication dispenser 1 with medication door 40 removed, to illustrate the view a person might typically have when readying to install a fresh aggregated medication pouch spool. FIG. 8 illustrates preferred embodiment medication dispenser 1 from a side sectional view, best illustrating the path a medication pouch spool will traverse during the dispensing process. As illustrated in these two Figures, the main housing is divided into two approximately vertically divided half-sections, right housing portion 30 and left housing portion 34. These right and left housing portions 30, 34 provide structure and protection for other components (e.g. camera 12, touch video display 10, speaker 26, microphone 16, etc.). The exterior of medication dispenser 1 including right and left housing portions 30, 34 is preferably fabricated from a variety of strong and durable materials, including but not limited to metals, metal alloys, particularly durable or "unbreakable" resins and plastics that may further be reinforced with various fibers, ceramics or cementitious materials, or even combinations, composites, or laminates of the above.

Medication pouch spool chamber 35 is formed as a generally cylindrical inset into left housing portion 34, and is configured to hold a medication pouch spool. In that regard, a medication spindle 46 is securely anchored within the general center of medication pouch spool chamber 35 and extends out toward medication door 40. When a person is ready to install a fresh aggregated medication pouch spool into preferred embodiment medication dispenser 1, they will first hold the fresh aggregated medication pouch spool adjacent and in the viewing field of front camera 12. Front camera 12 is preferably configured to read one or more of medication date and time text imprint 72 machine readable indicia 74, and either automatically through web enabled communications or through a caregiver confirm that the aggregated medication pouch spool is correct for the intended patient. In alternative embodiments, such confirmation may be accomplished using other suitable means including but not limited to separate and distinct readers such as handheld barcode readers or waiting to confirm using the readers internal to preferred embodiment medication dispenser 1 and described herein below.

Once confirmed, or if confirmation will occur subsequent to loading, the person next opens medication door 40. They may then simply slide the fresh aggregated medication pouch spool onto medication spindle 46, arranged in the manner best shown in FIG. 8 by spool unwind path 49. The spool will be arranged so that the exposed end of the spool is slipped between spool guide 48 and the outer diameter or wall of medication pouch spool chamber 35. The spool will then preferably be slightly unwound, directing the free end of the aggregated medication pouch ribbon, tape, or strip into spool outlet 38. The free end of the spool will be prevented from wrapping back around medication spindle 46 by rear packet feeder guide 180. Rear packet feeder guide 180 guides the free end of the spool into conveyor lower front rollers 121 and conveyor upper front rollers 122, as will be described in greater detail herein below with regard to FIGS. 10-15. From there, the free end of the spool travels through cutter assembly 100 to conveyor lower rear rollers 123 and conveyor upper rear rollers 124. After being cut by guillotine 112, again as described in greater detail herein below, a cut-off portion of the spool representing a medication pouch ready to be consumed passes through medication door 24 and drops into medication pouch basin 22.

While in preferred embodiment medication dispenser 1 the medication spindle 46 is horizontally oriented and longitudinally extensive in a direction perpendicular to the vertical plane defined by section line 8' in FIG. 3, it will be understood that medication spindle 46 may be oriented in any suitable manner. Where required due to spindle orientation, the unwound portion of the aggregated medication pouch spool may twist during or subsequent to unwinding. Likewise, while manual loading of an aggregated medication pouch spool is illustrated, it will be understood that in alternative embodiments an automatic loader similar to those used in handling film reels and film strips may be used to automatically load aggregated medication pouch spools.

As best illustrated in FIG. 8, a medication basins imaging device 28 for exemplary and non-limiting purposes comprises a short focal length video camera permitting clear viewing just a few inches away and further has a sufficient depth of field to provide clear focus on objects resting within medication basin 20 and medication pouch basin 22. Medication basins imaging device 28 will preferably have a field of view defined in a rearward direction by medication basins camera lower sight path 62 and in a forward direction by medication basins camera upper sight path 60, the exact field of view and directional limits which will be determined by a designer after review and consideration of the present disclosure and objectives.

A medications basin 20 sight path 61 is also illustrated. The maximum angle of medications basin 20 side walls is preferably limited to not create a shadow or non-visible region outside of view of medication basins imaging device 28. Consequently, to preserve the sight line, the steepest angle for the rear wall of medications basin 20 is limited by sight path line 61. As evidenced by the Figures, a preferred embodiment medication basin 20 is entirely open from above, in front, and both sides to allow easy insertion of individual medications from above, and easy removal of the individual medications as well. A large opening above the junction between medication basin 20 and medication pouch basin 22 allows a person to easily insert their hand into the space above medication pouch basin 22 to easily remove a pill pouch therein.

Front camera 12 is preferably mounted at some elevation above medication basin 20, as illustrated adjacent a top of preferred embodiment medication dispenser 1 distal to medication basin 20, and as a result may be provided with a longer distance focus than medication basins imaging device 28. This placement is desirable to enable front camera 12 to capture images of both a patient swallowing medications and also the space at least in front of and above medication basin 20, if not including a view directly into medication basin 20.

For exemplary purposes only, and not solely limiting the present invention thereto, front camera 12 has a lower sight path 66 that defines a rearward limit to the field of view approximately to the front edge of medication basin 20, and an upper sight path 64 that defines a forward limit to the field of view sufficiently high to capture even a relatively taller patient when swallowing one or more medications. Most preferably, and in accord with the teachings of the present invention, front camera 12 lower sight path 66 and medication basins camera upper sight path 60 either overlap or come sufficiently close to overlapping in field of view to track a patient's hand and fingers between the two cameras throughout or nearly entirely throughout the path of movement between retrieving medications from within one of the medication basins 20, 22 entirely to the patient's mouth. In some embodiments the field of view of the two cameras 12, 28 will not overlap. Nevertheless, the field of view will preferably be sufficiently close if not overlapping that it would either be extremely difficult or entirely impossible for a patient or would-be medication diverter to deceive the cameras and somehow remove the medication and replace or otherwise remove it from the patient's hand while within the gap between the two fields of view.

Said another way, the two images produced by the two cameras 12, 28 are sufficiently linked both spatially and in time to enable either a caregiver or an automated system to reliably validate the patient's removal of an aggregated medication pouch 70 from medication pouch basin 22. In the preferred embodiment, this is achieved by providing the two cameras 12, 28 with overlapping or immediately adjacent functional fields of view, or otherwise configured to allow a caregiver, whether a person or automated apparatus, to follow the patient's hand and arm simultaneously across both cameras, with any blind spots sufficiently small to provide a substantially complete deterrence against diversion of medication. While in some alternative embodiments, more than two cameras may be provided to validate the patient's removal of an aggregated medication pouch 70 from medication pouch basin 22, these additional cameras increase the complexity of data storage, data transmission, image analysis, and medical records archiving. Consequently, proper placement of the two imaging apparatuses 12, 28 with controlled access to ensure the imaging apparatuses capture the required image record is most preferred.

The functional field of view required favors a short focal length for medication basins imaging device 28, and a longer focal length for front camera 12. In alternative embodiments, particularly where the provide access from multiple directions, additional cameras are provided to record images sufficient to monitor access from each access direction. Preferably, no blind spots exist that are large enough to allow deception in movements or different hands, etc.

An audio speaker 26 may be provided mostly hidden within the space above medication door 24, also as best visible from FIG. 8, though the location of speaker 26 is not critical to the present invention. In addition, a medication basins light 29 is preferably located above medication pouch basin 22 and positioned to most preferably illuminate both medication basin 20 and medication pouch basin 22.

While the placement within preferred embodiment medication dispenser 1 is not critical, an optional backup battery door 36 is provided within medication pouch spool chamber 35. Batteries installed in a battery compartment behind backup battery door 36 provide operational power to preferred embodiment medication dispenser 1 in the event of a power line failure or an accidental or intentional disconnection of power plug 50 from a wall outlet.

Figure 9:
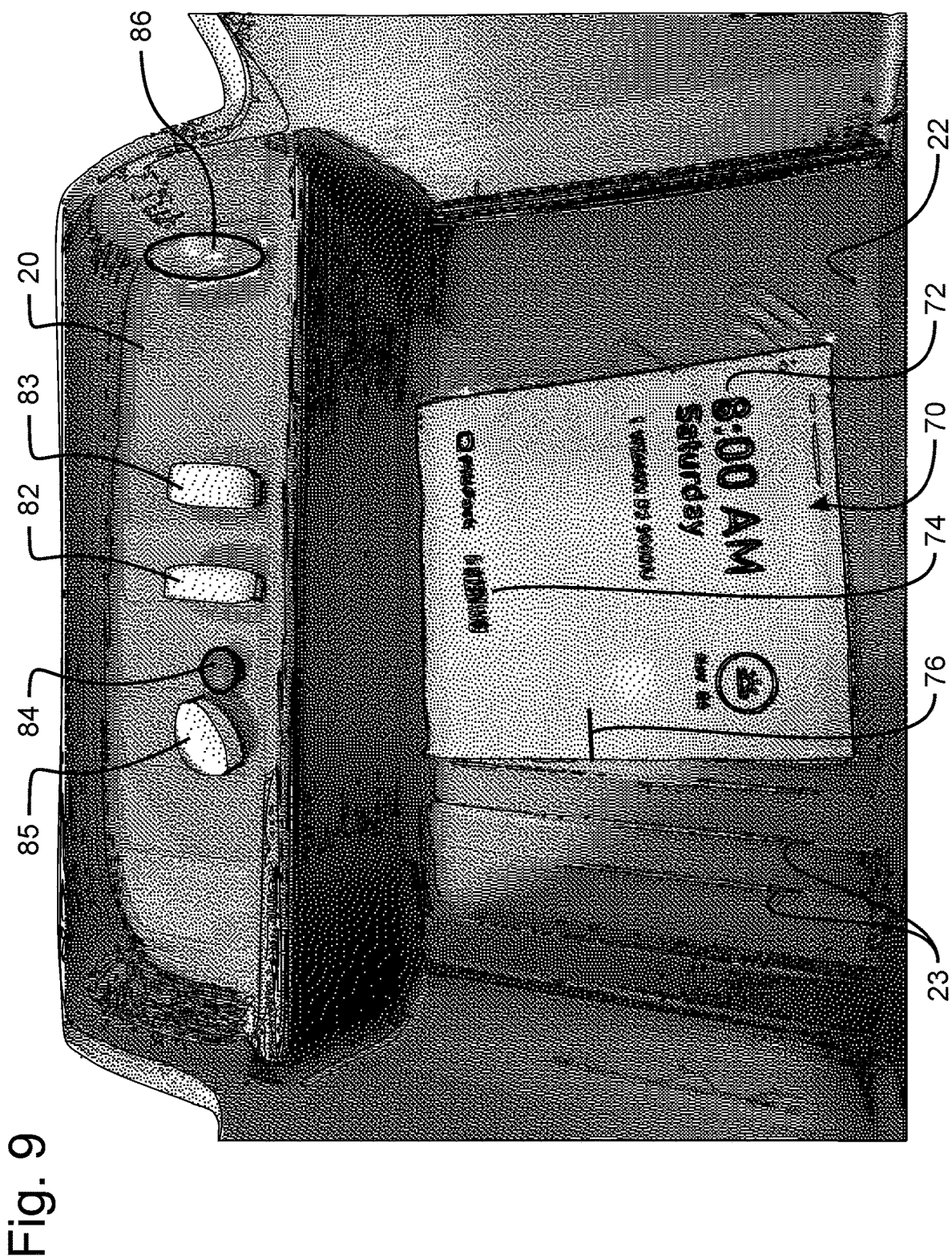
FIG. 9 illustrates an exemplary image of the medication basin and medication pouch basin generated by the medication basins camera.

FIG. 9 illustrates an exemplary image of medication basin 20 and medication pouch basin 22 generated by medication basins imaging device 28. While illustrated as being of monochrome format and relatively low resolution in order to comply with Patent Office drawing requirements, it is understood herein that in a preferred embodiment images generated by medication basins imaging device 28 will be in color to enable a viewer to identify color-coded medications, and also will have sufficient resolution to enable a viewer to read identifying imprints or indicia stamped or otherwise formed in or on medications. Nevertheless, in alternative embodiments a designer will select from other known imaging formats or resolutions desired and suitable for implementation of the present invention.

Visible in FIG. 9 is an exemplary aggregated medication pouch 70 having a medication date and time text imprint 72 that provides a patient or caregiver information necessary to confirm the date and time that aggregated medication pouch 70 should be consumed by the patient. A machine readable indicia 74, which for exemplary and non-limiting purpose may comprise a barcode, RFID tag, or other machine readable indicia, is provided. Machine readable indicia 74 may for exemplary and non-limiting purpose encode additional information such as a patient identifier that may be used to confirm the intended patient.

An optional slit 76 is illustrated within the side edge seal of aggregated medication pouch 70. In some embodiments slit 76 will be configured to extend entirely through the edge seal and into the interior of aggregated medication pouch 70. Slit 76 is preferably configured to facilitate opening, so that a person may more readily open aggregated medication pouch 70 and remove the medications therefrom. Consequently, the location of slit 76 is not critical to the invention, nor is the present invention solely limited to a slit. Any apparatus or treatments that facilitate opening of aggregated medication pouch 70 will be considered to be incorporated herein. Nevertheless, and as will be explained in greater detail herein below, guillotine 112 is configured in some embodiments to produce slit 76.

In accord with the teachings of the present invention, aggregated medication pouch 70 is packaged subject to quality assurance controls provided at the packaging facility. In addition, and again in accord with the teachings of the present invention, patient information is also confirmed by reading machine readable indicia 74 and confirming the patient is correct.

Most preferably, touch video display 10, front camera 12, microphone 14, speaker 26, medication basins imaging device 28, medication basins light 29, medication door 40, medication door locks 42, 43, and conveyor cutter 100 are electrically coupled or otherwise interconnected via web link circuitry such as taught in patents commonly owned with the present invention incorporated herein above by reference, including U.S. Pat. No. 9,202,011 by Lavin, entitled "Web enabled audiovisual medication dispensing"; 10,078,732 by Lavin, entitled "Web enabled audiovisual medication dispensing"; and 10,347,377 by Lavin, entitled "Web enabled audiovisual medication dispensing" and other patents and publications incorporated by reference herein above. Web access enables ready fulfillment of a number of validation and compliance steps outlined herein, including access to pharmaceutical databases and electronic health care records. While communications through a web link is most preferred, additionally providing much flexibility and nearly universal access amongst persons and devices, those skilled in the electrical communications arts will recognize that many other communications links are also well-known equivalents that provide more specific and dedicated functions. Such equivalents are considered incorporated herein and for the purposes of the present disclosure will be understood to be web links to provide web enabled dispensing, and will be used in some alternative embodiments where wider access and more diverse devices are not required.

The web link circuitry is preferably configured for bidirectional video and audio communications with a remote device such as a smartphone, computer, and the like, to permit video conference communication between a caregiver and a dependent. The web link circuitry may be coupled to a caregiver's phone or computer through 3G, 4G, 5G, wireless, wired, telephonic, or other means of electrical signal transmission. The web link circuitry may be configured to transmit images to touch video display 10, and the touch video display 10 may be configured to display the images received from the web link circuitry. In some embodiments, touch video display 10 may also be used to show images selected by the caregiver, such as images of medications or reminders.

In some embodiments, the web link circuitry may be programmed using touch video display 10. In some embodiments, web link circuitry may be configured to transmit data from front camera 12, medication basins imaging device 28, and microphone 14 to a caregiver's smart phone, and receive data from the caregiver's smart phone and transmit the data from the smart phone to touch video display 10, speaker 26, or conveyor cutter 100. In certain examples, web link circuitry may be configured to allow only authorized users to establish communication using preferred embodiment medication dispenser 1.

Patient identification may for exemplary and non-limiting purpose include: visual recognition of the image of the patient present within front camera 12 by a caregiver or other person who knows the patient and who can then confirm the patient's identity, or through comparison with photographic records; biometric data analysis which for exemplary and non-limiting purpose may include fingerprint patterns, facial characteristics, voice recordings, retinal patterns, and the like; or other patient identification information techniques, for exemplary and non-limiting purposes such as described in the various patents and published applications incorporated herein above by reference. The medication date and time text imprint 72 is also visible to a caregiver, other person, or automated system, and can thereby also be confirmed to be appropriate. Consequently, for some patients and prescribed medications, no further validation will be required and the patient may open and directly consume the medications found within aggregated medication pouch 70. However, for other patients or for more highly controlled medications, it may be necessary to provide further medication compliance validation and confirmation.

Pills 82-85 of various geometries and a liquid-filled capsule 86 are also visible in FIG. 9, the particular type and quantity which will in most cases be determined by a physician or pharmacy. Owing to the orientation of the aggregated medication pouch 70, with the opaque side having the medication date and time text imprint 72 on the top visible surface, a person or automated system reviewing the image generated by medication basins imaging device 28 and illustrated in FIG. 9 cannot confirm that there are any contents within aggregated medication pouch 70. In accord with the preferred embodiment of the invention, a patient will first reach into medication pouch basin 22 and remove aggregated medication pouch 70 therefrom. The patient will then open the interior of aggregated medication pouch 70, such as by tearing the pouch at slit 76. Owing to the overlapping imaging provided by medication basins imaging device 28 and front camera 12, a caregiver or other person or automated apparatus viewing these images can follow the movement of aggregated medication pouch 70 and the release of medications held therein into medication basin 20.

Once medications such as pills 82-85 of various geometries, liquid-filled capsule 86, and any other solid or gelled medications delivered in an aggregated medication pouch 70 have been dropped or otherwise delivered into medication basin 20, the caregiver or other person or automated apparatus viewing these images can validate the expected contents of aggregated medication pouch 70. This medication validation can take many forms and provide many different levels of security and certainty, depending upon the needs of a particular patient and prescribed medications.

For exemplary and non-limiting purposes, in a most basic implementation a patient, caregiver, medical practitioner, or automated system may simply count the number of medications visible within medication basin 20, presuming medication basin 20 was confirmed to be empty prior to dispensing the contents of aggregated medication pouch 70 into medication basin 20. In some embodiments, medication dispenser 1 will therefore require a patient to empty medication basin 20 prior to actuating and dispensing an aggregated medication pouch 70. While medication validation by verification of count is extremely simple for either a person or automated system, this may be adequate validation for many patients.

In a slightly more complex but also more thorough medication validation, a caregiver or medical practitioner familiar with either the patient and medications or familiar with identification and confirmation of medications may provide visual confirmation that the expected medications are present within the image provided by medication basins imaging device 28. In such case, the patient may then be advised to proceed with consuming each of the individual pills 82-85 of various geometries, liquid-filled capsule 86, and any other solid or gelled medications delivered in an aggregated medication pouch 70 and resting within medication basin 20.

Alternative embodiment medication validation may include sequentially presenting images of each expected medication and associated number of pills to a patient, caregiver, other person, or automated system. The person or automated system may visually or optically confirm that these expected medications and counts are in fact resting within medication basin 20. Other known techniques such as color, size, weight, and medication indicia are used in yet other embodiments to further identify and validate the contents of an aggregated medication pouch 70, the extent of such validation which, as noted herein above, will be determined for each patient and types of medications contained within an aggregated medication pouch 70.

In some embodiments of the invention, other medications in addition to medications and other products or consumables contained within an aggregated medication pouch 70 are also imaged. Such medications may include, for exemplary and non-limiting purposes, Over-The-Counter (OTC) medications such as aspirin, allergy medications, prescriptions that may be consumed on demand, various adjuncts, herbals, vitamins, and personal care products, and the like. In such embodiments, these other products or consumables may also be placed into medication basin 20 for identification and compliance validation, or alternatively displayed by a patient or caregiver in front camera 12 for compliance validation. Such compliance validation may include not only that the expected medications have been dispensed and are ready for patient consumption, but where web enabled and particularly with automated medication validation, the collective medications and other products about to be consumed will in some embodiments be checked to determine whether there are any known drug contraindications or special consumption requirements, such as whether individual medications may be taken together or must be taken in different ways, sequence, or at slightly different times rather than all at once.

In some further alternative embodiments of the invention, optional visual monitoring of other medications may be provided through one or more separate and additional imaging apparatus. In one exemplary embodiment, a separate station is provided that is monitored by a separate imaging apparatus such as but not limited to a video camera for liquid prescriptions and other supplements, adjuncts, and the like that are not readily packaged in an aggregated medication pouch 70. In some of these embodiments, the separate station is configured to affix or attach through suitable apparatus to preferred embodiment medication dispenser 1, and an imaging apparatus suitable for monitoring the separate station is provided within preferred embodiment medication dispenser 1.

While in the preferred embodiment medication dispenser 1 as illustrated the imaging of an entire pouch resting within medication pouch basin 22 occurs from above using pouch medication basins imaging device 28, it will be understood herein that one or more additional imaging apparatuses may be provided to capture an image from the bottom side or other suitable angle of the pouch at any location in the conveyance process where such image can be confirmed to associate directly with a delivered aggregated medication pouch 70 delivered into medication pouch basin 22. In such case, a patient would not be required to tear open the package and subsequently deposit the medications within the medication basin 20. Instead, and using the additional imaging apparatus, medications may be viewed by a remote apparatus or person such as a caregiver directly through the transparent side of aggregated medication pouch 70 when such transparency is available.

In some embodiments this is accomplished by imaging through the transparent side of aggregated medication pouch 70 while in transit. However, this transitory imaging of individual medications is at best very difficult to work with and generally unreliable. In other embodiments, the in-transit imaging is of the medication date and time text imprint 72, machine readable indicia 74, and optional slit 76. In such embodiments and in contradistinction to the illustration of FIG. 9, when aggregated medication pouch 70 is dispensed into medication pouch basin 22 the transparent side is up. For exemplary and non-limiting purpose, this in turn means that exemplary pills 82-85 and liquid-filled capsule 86 are visible in the image of medication pouch basin 22 provided by medication basins imaging device 28. Unfortunately, in some cases even if an image is taken from the transparent side, from opposed sides, or at several angles, different sizes and types of medications contained with a single aggregated medication pouch 70 may conceal or otherwise interfere with the accurate identification of each and every medication that has been prescribed. Consequently, in preferred embodiment medication dispenser 1, the contents of aggregated medication pouch 70 are preferably displayed within medication basin 20. In some embodiments, medication basin 20 is also partially or entirely transparent or provided with imaging holes or openings. In such embodiments, one or more imaging apparatuses are provided to capture images from the bottom, sides, or other angles to provide additional information selected to improve the accurate identification or validation of medications resting therein.

One of the benefits of using a spool of aggregated medication pouches 70 to dispense medications is the ability of the preferred embodiment medication dispenser 1 to dispense individual aggregated medication pouches 70 for those times where a patient will be traveling, whether for day trips or for more extended periods. For exemplary and non-limiting purpose, if a patient will be vising a doctor for a several hour appointment, an appropriate number of aggregated medication pouches 70 are dispensed to cover the period of separation of the patient from preferred embodiment medication dispenser 1. Nevertheless, during this extra dispensation, some of the benefits of preferred embodiment medication dispenser 1 are preserved including validation of the medication date and time text imprint 72, machine readable indicia 74, recording of the patient receiving the dispensed aggregated medication pouches 70, and, where provided, even the presence and size of optional slit 76.

In some embodiments, optional ribs 23 for exemplary and non-limiting purpose illustrated in FIG. 9 are provided that extend at least partially across the center region of medication pouch basin 22. Ribs 23 are configured to facilitate grasping of an aggregated medication pouch 70. When located solely more centrally within medication pouch basin 22 and not extending to the edges, ribs 23 will elevate one or more of the edges of aggregated medication pouch 70 above the bottom of medication pouch basin 22, making it easier and more convenient for a person to manually grasp the edge of the pouch. In some embodiments, similar ribs or other features may be provided within medication basin 20. Medication basins 20, 22 may be provided with coatings, surface treatments, or the like designed to facilitate proper insertion and removal of aggregated medication pouches therein.

In some embodiments, a variety of sensors and imaging apparatuses may be provided to monitor one or more portions of preferred embodiment medication dispenser 1, such as but not limited to the integrity of the exterior components and locks, an aggregated medication pouch spool, and the individual aggregated medication pouches 70. In some of those embodiments, one or more of the sensors will be web-enabled, to permit remote alerting, review, or monitoring.

Figure 10:
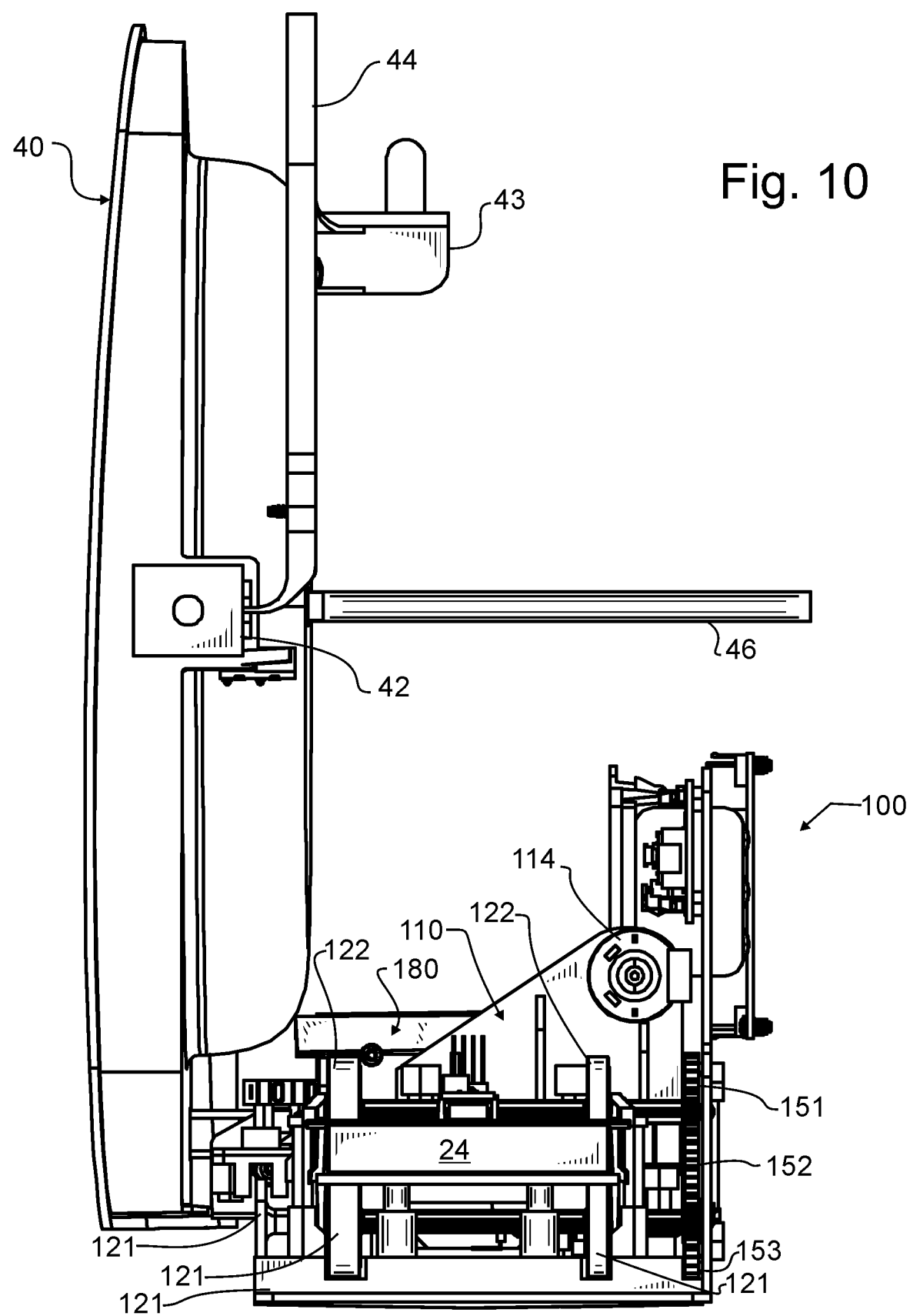
FIG. 10 illustrates a preferred embodiment conveyor, cutter, medication spindle, and medication door used within the preferred embodiment web enabled audiovisual medication dispensing apparatus with enhanced compliance verification of FIG. 1 from a front elevational view, with the housing, touch screen, and other components removed for illustrative purpose.
Figure 11:
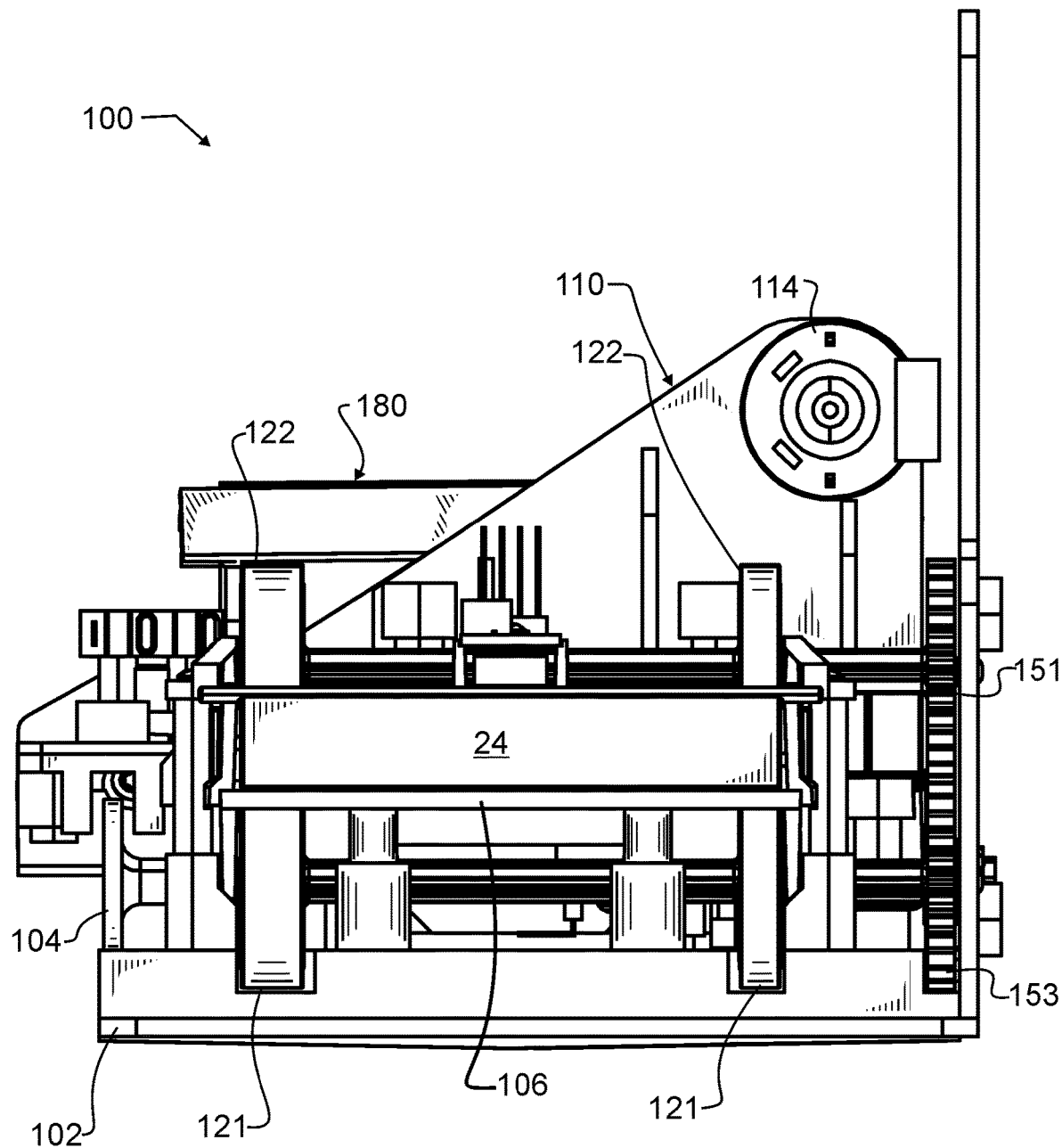
FIG. 11 illustrates the preferred embodiment conveyor and cutter of FIG. 10, with the medication spindle and medication door also removed for illustrative purposes, from a front elevational view.

FIGS. 10-15 illustrate conveyor cutter 100 in greater detail. In FIG. 10 medication door 40 is also included, to illustrate medication door locks 42, 43. Locks 42, 43 both have a default position of closed. Upon appropriate electrical or other impulse triggering a solenoid, linear or rotary actuator or other suitable actuator, medication door lock bar 44 releases locks 42, 43 allowing for medication door 40 to be opened. In some embodiments, this may be achieved when preferred embodiment medication dispenser 1 is at the pharmacy, so that an aggregated medication pouch spool can be loaded onto medication spindle 46. Once the medications are loaded onto the medication spindle 46, the spool leading and free end aggregated medication pouch 70 can be fed into conveyor cutter 100.

Once the spool leading and free end aggregated medication pouch 70 is properly engaged with conveyor cutter 100, medication door 40 can be closed. Preferred embodiment medication dispenser 1 is ready to be picked up by the patient. Alternatively, preferred embodiment medication dispenser 1 can be unlocked, loaded, and closed by a home healthcare worker or other person certified or authorized to do so. Where medication door locks 42, 43 are electromechanically controlled and web-enabled, access to the aggregated medication pouch spool may be controlled and enabled selectively to suit any required medicine compliance protocols.

Once loaded, preferred embodiment medication dispenser 1 can be used by a patient. Prior to dispensing one or more aggregated medication pouches 70 to the patient, a machine reader such as barcode reader 184 reads machine readable indicia 74. In the preferred embodiment as illustrated in FIG. 9 machine readable indicia 74 is a barcode. The machine readable indicia 74 preferably incorporates data sufficient to allow confirmation that the right aggregated medication pouch 70 is being dispensed. Alternatively or additionally, an OCR reader 186 may read medication date and time text imprint 72 imprinted on aggregated medication pouch 70. After aggregated medication pouch 70 has been confirmed to be for the correct patient at the current time, the next action occurs within cutter assembly 110 to sever and dispense one or more of the aggregated medication pouches 70.

Conveyor cutter 100 has a base plate 102 to which all of the conveyor cutter 100 components are ultimately secured to. Base plate 102 is designed to provide rigid support to all the components of conveyor cutter 100 and ensure that the components above base plate 102 do not shift.

Aggregated medication pouches 70 within the spool are sequentially fed into rear packet feeder guide 180 and through the rear rollers 123, 124. Upper rear roller 124 is powered through upper rear gear 154 which is connected to lower rear gear 155. Lower rear gear 155 powers lower rear roller 123. By using the gears to transfer power to each other, they counter rotate, causing the rollers to push any aggregated medication pouch 70 through uniformly.

Cutting motor 114 turns motor gear 115, which in turn engages with guillotine gear 116, thereby lifting guillotine 112 up about guillotine pivot 118. This clears the dispensing pathway, so that the leading or next-to-be-dispensed aggregated medication pouch 70 can be moved forward and into dispensing position. Subsequently, gears 151, 152, 153, 154, 155 are driven by any suitable means to pull the aggregated medication pouches from medication spindle 46 through rear packet feeder guide 180 by rear rollers 123, 124 and forward to front rollers 121, 122. In some embodiments, front rollers 121, 122 pull at a slightly faster rate than rear rollers 123, 124, thereby tensioning the leading or next-to-be-dispensed aggregated medication pouch 70 therebetween.

While in preferred embodiment medication dispenser 1 the rollers 121-124 engage generally with the side edges of an aggregated medication pouch 70 as best illustrated in FIGS. 10, 11, 13, and 15, other suitable driving mechanisms may be provided and are considered incorporated herein. Some alternative embodiment drive mechanisms include, for exemplary and non-limiting purpose, toothed wheels similarly engaging with the side edges, and belts or soft elastomeric rollers that engage with a substantial portion of the major surfaces of an aggregated medication pouch 70.

Figure 12:
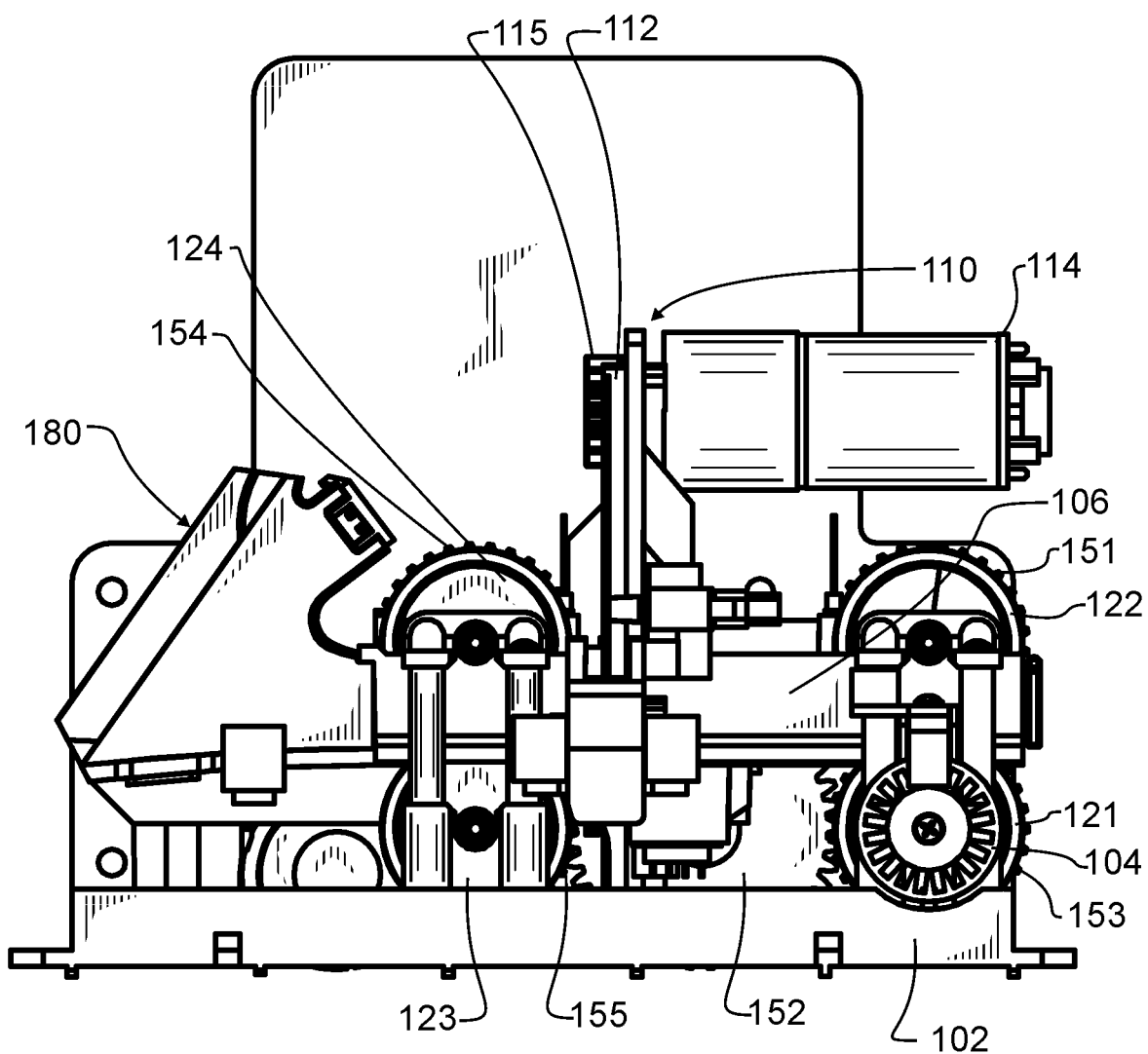
FIG. 12 illustrates the preferred embodiment conveyor and cutter of FIG. 11 from a left side elevational view.

Conveyor measurer 104, which may for exemplary and non-limiting purpose comprise a rotary encoder as best illustrated in FIG. 12, preferably provides one affirmation that gears 151, 152, 153, 154, 155 are turning. Conveyor measurer 104 will also preferably provide a measure of distance that a leading aggregated medication pouch 70 will have moved under the influence of rollers 121-124, to predictively locate the pouch within cutter assembly 110.

In addition or alternatively thereto, one or more barcode readers or other type of optical sensors 184, 186 will detect a suitable feature within, on or imprinted upon aggregated medication pouch 70. For exemplary and non-limiting purpose, such feature may be the leading or trailing edge of aggregated medication pouch 70, a line extending partially or entirely transversely across aggregated medication pouch 70, medication date and time text imprint 72, machine readable indicia 74, or other appropriate feature.

Once the leading or next-to-be-dispensed aggregated medication pouch 70 is determined to be located in the proper position, and whether such proper position is confirmed by rotary encoder 104 or other type of sensors, gears 151, 152, 153, 154, 155 stop. Presuming barcode reader 186 has also confirmed that the right pouch has made it to the front side of cutter assembly 110, which may be done before movement into final position, during movement, or after stopping in final position, then cutting motor 114 activates and drives guillotine 112 down, thereby severing aggregated medication pouch 70 from the remaining spool.

While a guillotine-type cutter is described herein in accord with the preferred embodiment of the invention, other suitable types of cutters or severing apparatus may be used herein. For exemplary and non-limiting purpose, alternative embodiment cutters include scissors, a roller cutter, one or more knives, one or more hot bars configured to melt through the plastics used to define each pouch, a thermal laser such as an Infra-Red (IR) laser, and an ablative laser such as an Ultra-Violet (UV) or excimer laser. Other types of severing apparatus are also considered incorporated herein, including for exemplary and non-limiting purpose differential gearing between rear rollers 123, 124 and front rollers 121, 122 designed to sever perforations or other types of lines of weakness between individual aggregated medicine pouches, and other similar or otherwise suitable severing apparatus.

Once at least one aggregated medication pouch 70 has been separated from the spool, then in a preferred embodiment transfer gear 152 disengages from rear gears 154, 155 and drives the separated aggregated medication pouch 70 out through medication door 24 into medication pouch basin 22. Conveyor measurer 104 for exemplary and non-limiting purpose is used to determine how far conveyor upper front rollers 122 have turned. By measuring conveyor upper front rollers 122 when transfer gear 152 is engaged to the rear gears 154, 155 the distance aggregated medication pouch 70 has traveled forward can be measured so guillotine 112 will cut aggregated medication pouch 70 at the desired location. Then after the transfer gear 152 is disengaged from the rear gears 154, 155 conveyor measure 104 is used to make sure the aggregated medication pouch 70 clears medication door 24. By applying sufficient forward speed to aggregated medication pouch 70, momentum will carry it from medication door 24 into medication pouch basin 22.

In preferred embodiment medication dispenser 1, medication door 24 is weighted and retained in position solely under the force of gravity. However, in alternative embodiments such as those requiring greater levels of medication security, medication door 24 may be electromagnetically opened and closed, such as with a solenoid, linear, or rotary actuator drive. Furthermore, in some embodiments medication door 24 may be displaced away from being immediately adjacent to the opening into medication pouch basin 22, thereby limiting access to medication door 24.

An additional tamper resistant feature optionally provided in a preferred embodiment is guillotine 112. Guillotine 112 as described herein above is configured to stay in a lowered position when preferred embodiment medication dispenser 1 is not authorized to dispense. As a result, guillotine 112 acts as a barrier helping to prevent a patient or would-be medication diverter from forcing medication door 24 open and sticking their fingers or other implements into medication dispenser 1 to grab additional aggregated medication pouches and pull them out of medication door 24. Other types of cutters capable of creating a similar barrier will likewise provide similar benefit when in a closed position, creating a barrier that limits access to the free end of an aggregated medication pouch 70.

To better facilitate the manual opening of an aggregated medication pouch 70, in some embodiments optional slit 76 is provided and extends entirely within the side edge seal of aggregated medication pouch 70, and not into the interior of the pouch. In some other embodiments, slit 76 is provided and is configured to extend entirely through the edge seal and into the interior of aggregated medication pouch 70, such as illustrated for exemplary purpose in FIG. 9.

To produce slit 76, sensors such as conveyor measurer 104 and optical sensors 184, 186 are used to further locate a position of an aggregated medication pouch 70 relative to guillotine 112 at some position intermediate between the leading and trailing edges of the pouch. In these embodiments, aggregated medication pouch 70 is stopped twice. Aggregated medication pouch 70 is first stopped at a position intermediate relative to guillotine 112, and guillotine 112 is only partially actuated. As may be appreciated, guillotine 112 first cuts aggregated medication pouch 70 along a side edge, and then when further actuated progressively cuts from edge to edge. When in this position intermediate relative to guillotine 112, guillotine 112 is only partially actuated to create slit 76 of length determined by a designer after review of the present disclosure. Aggregated medication pouch 70 is then advanced, and is stopped a second time, this time at a position relative to guillotine 112 such that guillotine 112 will cut through a trailing edge of aggregated medication pouch 70 without cutting into the interior of the pouch. This second time, guillotine 112 is fully actuated such that guillotine 112 will sever aggregated medication pouch 70 from the remaining aggregated medication pouch spool. In some embodiments, the length and optionally the location of slit 76 can be validated by medication basins imaging device 28.

Figure 13:
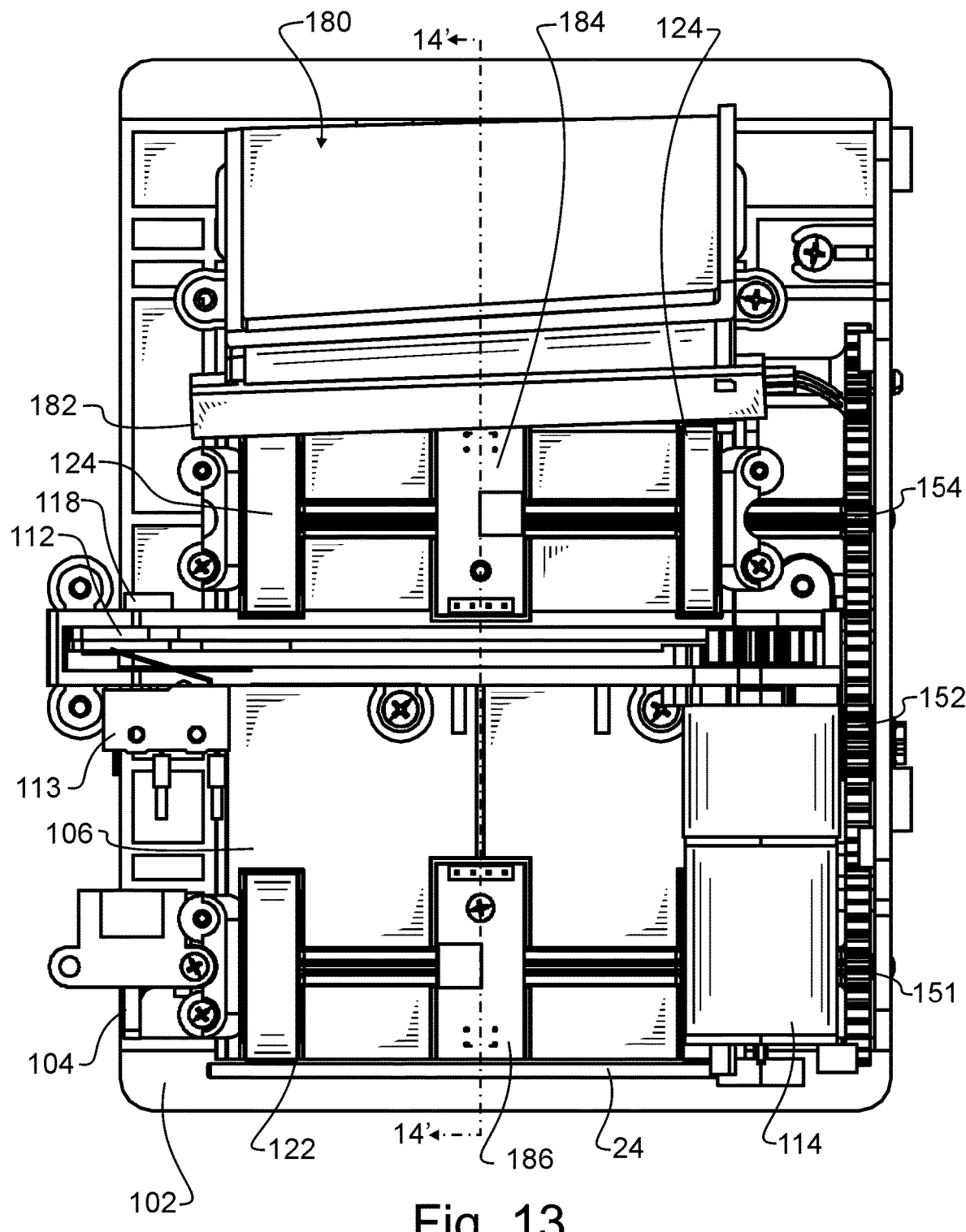
FIG. 13 illustrates the preferred embodiment conveyor and cutter of FIG. 11 from a top plan view.
Figure 14:
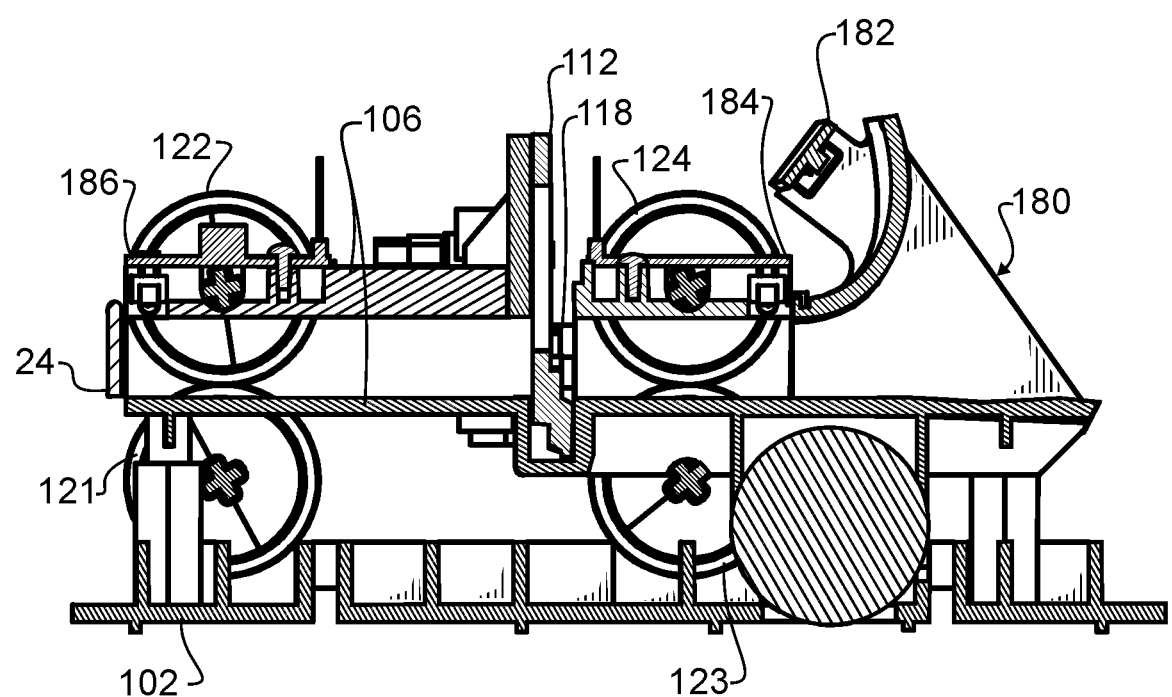
FIG. 14 illustrates the preferred embodiment conveyor and cutter of FIG. 11 from a sectioned side view sectioned along line 14' in FIG. 13.
Figure 15:
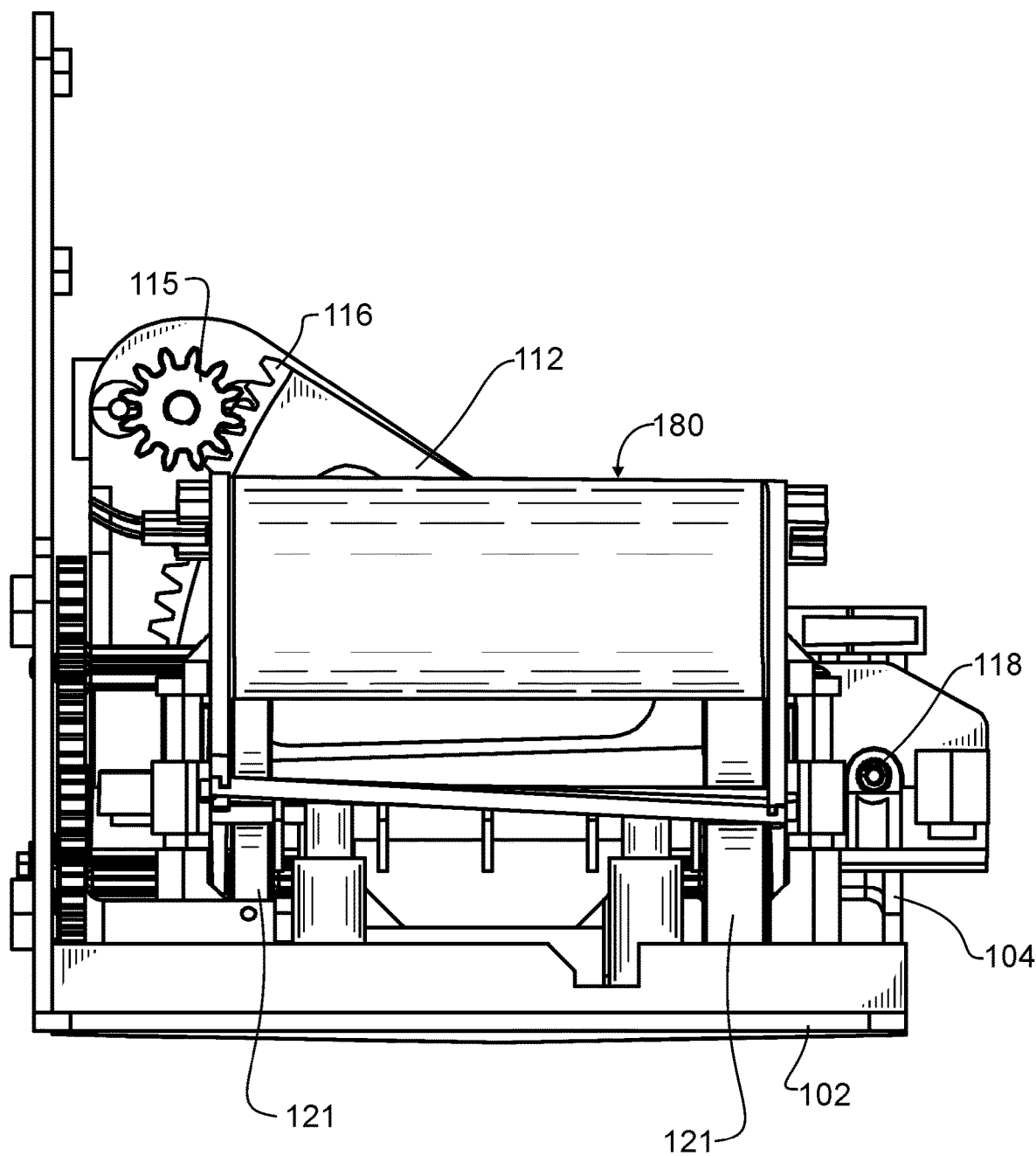
FIG. 15 illustrates the preferred embodiment conveyor and cutter of FIG. 11 from a rear elevational view.

Determination of an extent of actuation of guillotine 112 will in some embodiments be made entirely through electrical control of the actuation of cutting motor 114, as is well-known and documented in the field of stepper motor control. Nevertheless, in other embodiments additional sensors are provided. For exemplary and non-limiting purpose a micro-switch 113 is illustrated in FIG. 13, though a myriad of other suitable position sensors are known in the position sensing and servo-motor arts that are considered to be incorporated herein.

Once again, in other embodiments other types of cutters capable of creating a similar slit through one actuation and a full severing through a second actuation will likewise provide similar benefit and so will be understood to be incorporated herein. Such cutters will for exemplary and non-limiting purpose include scissors, a roller cutter, one or more knives, and one or more hot bars.

When slit 76 extends only partially through a side edge of aggregated medication pouch 70, and again ultimately dependent upon the geometry of a cutter, there is little but not a zero chance of damaging any medications that are adjacent to the edge of the pouch. As one example, if a relatively large medication is nestled against the edge of aggregated medication pouch 70, the thickness of the pouch may extend into a space that a cutter would occupy, even if only partially cutting a side edge. In such instance, there is some risk of damaging the medication.

Consequently, the geometry of a cutter must be carefully selected to be able to both partially cut a side edge of aggregated medication pouch 70 and still avoid contacting medications immediately adjacent the edge of the pouch. Some types of cutters are less prone to such interference, including but not solely limited to a steeply angled guillotine blade, scissors that pivot relatively close to the side edge of aggregated medication pouch 70, a small diameter roller cutter, a knife or hot bar that is steeply angled or relatively more perpendicular to the plane of aggregated medication pouch 70, and laser cutters.

In addition, the location of slit 76 in some embodiments will also be selected to reduce the possibility of contacting or damaging medications such as pills 82-85. While slit 76 is illustrated as being approximately midway between leading and trailing edges of aggregated medication pouch 70, if slit 76 is immediately adjacent to the leading or trailing edges, then any medications immediately adjacent thereto are most likely to be pushed away from the edge than damaged. Unfortunately, such placement of slit 76 also renders the slit more prone to deviating from tearing into the interior of aggregated medication pouch 70.

In some alternative embodiments, conveyor tube 106 is provided with one or more vertical axis rollers intermediate between conveyor rear rollers 123, 124 and conveyor front rollers 121, 122, and extending slightly into engagement with at least the side edge of aggregated medication pouch 70 that will be subsequently slit to produce slit 76. Such roller(s) in accord with the present invention will press against the side edges of aggregated medication pouch 70 sufficiently to push any medications immediately adjacent to the pouch side edge(s) away therefrom and more to the center of the pouch interior. In other alternative embodiments, at least one side vertical wall of conveyor tube 106 may be curved inward intermediate between conveyor rear rollers 123, 124 and conveyor front rollers 121, 122, extending slightly into engagement with the side edge(s) of aggregated medication pouch 70 for similar purpose and function. In these alternative embodiments, medications are moved away from one or both of the side edges, again reducing the likelihood of damage to medications such as pills 82-85 within aggregated medication pouch 70 during the formation of slit 76.

In preferred embodiment medication dispenser 1, aggregated medication pouch 70 is moved into position relative to guillotine 112. Nevertheless, in some alternative embodiments, a cutter such as guillotine 112 or alternative cutters as described herein above may be moved relative to conveyor tube 106 while aggregated medication pouch 70 stays in fixed position relative to conveyor tube 106. Further, in the case of a laser cutter, mirrors and other apparatus known in the laser arts and considered incorporated herein may be used to redirect the radiation to form desired cuts, slits, perforations, and the like.

In some embodiments of the invention, various ones of blood pressure meters, pulse oximeters, heart rate monitors, blood glucose monitors, fall monitors, smart watches, other wearables, smart phones, scales, and other known medical devices, meters, and sensors are incorporated and preferably integrated into preferred embodiment medication dispenser 1. In some embodiments of the invention, optional monitoring and tracking of other health regimens, for exemplary and non-limiting purposes various exercise or physical therapy activities, is incorporated and preferably integrated into preferred embodiment medication dispenser 1.

In some embodiments of the invention, one or more of patient validation, validation of presence of at least one aggregated medication pouch 70 within medication pouch basin 22, and validation of removal of at least one aggregated medication pouch 70 from within medication pouch basin 22 may in some embodiments occur within preferred embodiment medication dispenser 1. In such embodiments, appropriate analysis apparatus must be provided, such as taught for exemplary and non-limiting purpose in the references incorporated by reference herein above. In such embodiments, the data maybe stored internally and later transferred at a convenient time for medical record storage or validation compliance, either as a batch when web link connections are available or in some further alternative embodiments when preferred embodiment medication dispenser 1 is reloaded at a pharmacy or the like.

The preferred embodiment medication dispenser 1 combines front camera 12 and medication basins imaging device 28 with an aggregated medication pouch spool. Nevertheless, it will be appreciated by those reasonably skilled in the field that the present invention pertaining to the use of both a front camera 12 and medication basins imaging device 28 for validation may be used with many other types of semi- or fully-automated medication dispensers such as but not limited to those incorporated by reference herein above.

In a preferred embodiment, activation of front camera 12 and medication basins imaging device 28 is accomplished and controlled in accord with the teachings of our patents commonly owned with the present invention incorporated herein above by reference, including U.S. Pat. No. 9,202,011 by Lavin, entitled "Web enabled audiovisual medication dispensing"; 10,078,732 by Lavin, entitled "Web enabled audiovisual medication dispensing"; and 10,347,377 by Lavin, entitled "Web enabled audiovisual medication dispensing". Such activation and control, in some preferred embodiments herein further includes the ability for a remote caregiver to simultaneously view the images from front camera 12 and medication basins imaging device 28 while communicating verbally with the patient, the combination that greatly facilitates remote confirmation that the right person received the right medications at the right times and greatly facilitates documentation of medication compliance. Select ones or all of these images are preferably communicated to and stored within the patient's permanent electronic health record. The present preferred remote communication between a caregiver and a patient who might otherwise at least periodically fail to properly operate a semi-automated or automated medication dispenser renders much higher rates of successful adoption and implementation of the present invention. Furthermore, such levels of care provided by the present invention greatly reduce the need and number of in-person visits required for most patients, thereby simultaneously reducing the burden on a caregiver and reducing the financial and emotional costs of assistance while also simultaneously increasing the chance that the patient will remain both healthier and will safely stay in an independent home or less-assisted living facility.

The locked tamper resistant container provided within preferred embodiment medication dispenser 1 helps prevent individuals from taking too much of any medication by bypassing the dispensing schedule. Furthermore, the locked tamper resistant container also helps prevent medication diversion by someone to whom the prescription is not intended. Timers and alarms are preferably provided that allow for proper timing of the medication dispensing, and alert the patient that there are medications to take. This encourages the patient to take medications at the right time. The first imaging apparatus enables confirmation that the medication pouch or pouches were properly dispensed into the medication pouch receptacle. The second imaging apparatus enables confirmation that the medications are consumed.

Remote video and audio communication allows for a number of benefits. The first is a reviewable and independently confirmable compliance record of the person taking their medication. The second benefit is to ensure that the authorized person is the one taking the medication. A third benefit is to allow for modification of which pills to take if a scheduled period elapsed. If the medication was dispensed at the timer interval anyone who was present would be able to take the medication, whether it is the intended recipient or not. Thus, when needed, the remote video and audio communication allows for confirmation of the intended recipient of the medication before dispensing. As a fourth benefit, the records of the person taking the medication can be saved to ensure patient compliance with their medications and ensure legal compliance with any agencies.

While the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

We claim:

1. A web enabled audiovisual medication system with enhanced compliance verification, comprising in combination a web enabled audiovisual medication dispenser and a remote caregiver apparatus, said remote caregiver apparatus having:
    a microphone configured to capture audio input and transmit the audio input to said web enabled audiovisual medication dispenser;
    a speaker configured to receive an audio signal originating at said web enabled audiovisual medication dispenser and reproduce an audible output;
    a camera configured to capture images of a caregiver and transmit said images to said web enabled audiovisual medication dispenser; and
    a display screen configured to receive a video signal originating at said web enabled audiovisual medication dispenser and produce a visual display;
    said web enabled audiovisual medication dispenser having:
        a housing;
        web link circuitry configured to establish audiovisual communication with said remote caregiver device;
        a microphone electrically coupled to the web link circuitry and configured to capture audio input and transmit the audio input to the web link circuitry, and the web link circuitry configured to receive the audio input and transmit the audio input to a caregiver;
        a speaker electrically coupled to the web link circuitry and configured to receive an audio signal originating at said remote caregiver apparatus from said web link circuitry and reproduce an audible output;
        a display screen electrically coupled to the web link circuitry and configured to receive a video signal originating at said remote caregiver apparatus from said web link circuitry and produce a visual display;
        a medication pouch chamber enclosed within said housing;
        a plurality of medication pouches stored within said medication pouch chamber that each contain at least one medication;
        a medication pouch receptacle partially enclosed within said housing and configured to receive and hold at least one of said plurality of medication pouches;
        a dispenser configured to transfer said at least one of said plurality of medication pouches stored within said medication pouch chamber from said medication pouch chamber to said medication pouch receptacle;
        a first imaging apparatus generating an image of said medication pouch receptacle and configured to capture a medication pouch receptacle image of said medication pouch within said medication pouch receptacle and communicate said medication pouch receptacle image through said web link circuitry to said remote caregiver apparatus and further configured to capture a medication pouch removal image of at least a portion of a patient's hand during said patient's removal of said medication pouch from said medication pouch receptacle; and
        a second imaging apparatus having a functional field of view including at least a patient's hand, arm, and face and further including a medication handling region extending substantially between said patient's face to at least adjacent to said medication pouch receptacle, said second imaging apparatus configured to capture a first medication handling region image of said patient, and a second medication handling region image of said patient removing at least one medication from said at least one of said plurality of aggregated medication pouches, and a third medication handling region image of said patient consuming said at least one medication removed from said at least one of said plurality of aggregated medication pouches.

2. The web enabled audiovisual medication system of claim 1, wherein individual ones of said plurality of medication pouches each further comprise a pouch interior and a plurality of medications aggregated and sealed within said pouch interior.

3. The web enabled audiovisual medication system of claim 1, wherein said medication pouch receptacle comprises a basin, and said image of said medication pouch receptacle displays an entire interior of said medication pouch receptacle when said medication pouch receptacle is empty.

4. The web enabled audiovisual medication system of claim 1, further comprising a medication receptacle, said medication pouch receptacle and said medication receptacle each located within a functional field of view of said first imaging apparatus.

5. The web enabled audiovisual medication system of claim 4, wherein said medication receptacle comprises a basin, and said image of said medication pouch receptacle displays an entire interior of said medication receptacle when said medication receptacle is empty.

6. The web enabled audiovisual medication system of claim 5, wherein said image of said medication pouch receptacle is configured to enable identification of said at least one medication at said remote caregiver apparatus when said at least one medication is held within said medication receptacle.

7. The web enabled audiovisual medication system of claim 4, wherein said first imaging apparatus further comprises a functional field of view substantially consumed by said medication pouch receptacle and said medication receptacle.

8. The web enabled audiovisual medication system of claim 1, wherein said web link circuitry is configured to communicate said medication pouch removal image to said remote caregiver apparatus.

9. The web enabled audiovisual medication system of claim 8, wherein said web link circuitry is configured to communicate said first medication handling region image to said remote caregiver apparatus.

10. The web enabled audiovisual medication system of claim 9, wherein said medication pouch removal image and said first medication handling region image are displayed simultaneously and synchronized in time upon said remote caregiver apparatus display screen.

11. The audiovisual medication dispenser with enhanced compliance verification of claim 9, wherein said medication pouch receptacle is hand accessible from only a single direction.

12. The web enabled audiovisual medication system of claim 1, wherein said medication pouch receptacle is hand accessible from only a single direction.

13. The web enabled audiovisual medication system of claim 1, wherein at least one of said medication pouch receptacle image, said medication pouch removal image, and said first medication handling region image further comprises a plurality of sequential images.

14. The web enabled audiovisual medication system of claim 1, wherein said second imaging apparatus has a field of view including at least a portion of said patient's hand, wrist, and forearm when said first imaging apparatus has a field of view including at least a portion of said patient's fingers within said medication pouch basin.

15. The web enabled audiovisual medication system of claim 1, wherein said first imaging apparatus and said second imaging apparatus comprise overlapping fields of view.

16. The web enabled audiovisual medication system of claim 1, wherein said first imaging apparatus and said second imaging apparatus are linked so as to validate said patient removing medication pouch from medication pouch receptacle.

17. The web enabled audiovisual medication system of claim 1, further comprising electronic medical records storage, said medication pouch receptacle image, said medication pouch removal image, and said first medication handling region image stored in said electronic medical records storage.

18. An audiovisual medication dispenser with enhanced compliance verification, comprising:
   a housing;
   a medication chamber enclosed within said housing;
   a plurality of medications stored within said medication chamber;
   a medication receptacle partially enclosed within said housing and configured to receive and hold at least one of said plurality of medications;
   a dispenser configured to transfer said at least one of said plurality of medications stored within said medication chamber from said medication chamber to said medication receptacle;
   a first imaging apparatus generating an image of said medication receptacle and configured to capture a medication receptacle image of said medication within said medication receptacle and further configured to capture a medication removal image of at least a portion of a patient's hand during said patient's removal of said medication from said medication receptacle; and
   a second imaging apparatus having a functional field of view including at least a patient's hand, arm, and face and further including a medication handling region extending substantially between said patient's face to at least adjacent to said medication receptacle, said second imaging apparatus configured to capture a first medication handling region image of said patient, and a second medication handling region image of said patient consuming said at least one medication removed from said medication receptacle.

19. A method of validating and documenting that a patient has received medications prescribed to said patient within a prescribed time window, comprising the steps of:
   inserting at least one medication into at least one aggregated medication pouch;
   securely storing said at least one aggregated medication pouch within a medication pouch chamber located and fully enclosed within a medication dispenser housing;
   transferring said at least one aggregated medication pouch from said medication pouch storage chamber to an externally accessible medication pouch receptacle that is configured to receive and retain said at least one aggregated medication pouch and expose said at least one aggregated medication pouch to manual access;
   generating a first video image having a field of view substantially consumed by said medication pouch receptacle;
   generating a second video image synchronous in time with said first video image and having a field of view including at least a patient's hands, arms, and face and further including a medication handling region extending substantially between said patient's face to at least adjacent to said medication pouch receptacle;
   wherein said first and second video images capture said patient removing said at least one aggregated medication pouch from said medication pouch receptacle and subsequently capture said patient removing and consuming said at least one medication from said at least one aggregated medication pouch.

\* \* \* \* \*